United States Patent [19]

Peters et al.

[11] Patent Number: 5,024,668
[45] Date of Patent: Jun. 18, 1991

[54] RETROGRADE PERFUSION SYSTEM, COMPONENTS AND METHOD

[75] Inventors: Jeffrey L. Peters; Jeffrey L. Orth, both of Salt Lake City, Utah

[73] Assignee: Rocky Mountain Research, Inc., Salt Lake City, Utah

[21] Appl. No.: 5,092

[22] Filed: Jan. 20, 1987

[51] Int. Cl.$^5$ ............................................ A61M 29/02
[52] U.S. Cl. ................................... 606/194; 600/18
[58] Field of Search ................... 600/17, 18; 128/344, 128/346; 604/97, 101, 102, 49; 606/192, 194

[56] References Cited

U.S. PATENT DOCUMENTS

| | | | |
|---|---|---|---|
| 2,854,982 | 10/1958 | Pagano | 604/52 |
| 3,394,705 | 7/1968 | Abramson | 604/43 |
| 3,513,845 | 5/1970 | Chesnut et al. | 600/18 |
| 3,583,404 | 6/1971 | McWhorter | 604/43 |
| 3,592,183 | 7/1971 | Watkins et al. | 128/111.1 |
| 3,592,184 | 7/1971 | Watkins et al. | 128/111.1 |
| 3,726,281 | 4/1973 | Norton et al. | 604/43 |
| 3,902,492 | 9/1975 | Greenhalgh | 604/43 |
| 3,939,820 | 2/1976 | Grayzel | |
| 3,981,299 | 9/1976 | Murray | 604/43 |
| 4,014,317 | 3/1977 | Bruno | 608/17 |
| 4,098,275 | 7/1978 | Consalvo | 604/5 |
| 4,116,589 | 9/1978 | Rishton | 600/18 |
| 4,129,129 | 12/1978 | Amrine | 604/49 |
| 4,211,233 | 7/1980 | Lin | 128/241 |
| 4,301,797 | 11/1981 | Pollack | 604/4 |
| 4,459,977 | 7/1984 | Pizon et al. | 128/344 |
| 4,501,581 | 2/1985 | Kurtz et al. | 604/52 |
| 4,531,936 | 7/1985 | Gordon | 604/49 |
| 4,587,975 | 5/1986 | Salo et al. | 606/192 |
| 4,648,384 | 3/1987 | Schmukler | 600/18 |
| 4,689,041 | 8/1987 | Corday et al. | 128/344 |
| 4,723,549 | 2/1988 | Wholey et al. | 128/344 |
| 4,782,834 | 11/1988 | Maguire et al. | 606/194 |
| 4,787,388 | 11/1988 | Hofmann | 606/194 |

FOREIGN PATENT DOCUMENTS

0150960  1/1985  European Pat. Off. ............. 600/18

OTHER PUBLICATIONS

E. Ubel, "How Science is Saving Your Heart", Parade Magazine, Sep. 1983.
H. G. DeYoung, "State of the Heart", High Technology, May 1984.
S. Meerbaum et al., "Hypothermic Coronary Venous Phased Retroperfusion: A Closed-Chest Treatment of Acute Regional Myocardial Ischemia" Circulation, vol. 65, No. 7, Jun. 1982.
G. Smith et al., "Reduction in Infarct Size by Synchronized Selective Coronary Venous Retroperfusion of Arterialized Blood" (The American Journal of Cardiology, vol. 48, Dec. 1981).
V. Gott et al., "Retrograde Perfusion of the Coronary Sinus for Direct Vision Aortic Surgery" (Surgery, Gynecology & Obstetrics, Mar. 1957).
S. Gundry, "Modification of Myocardial Ischemia in Normal and Hypertrophied Hearts Utilizing Diastolic Retroperfusion of the Coronary Veins" (Journal of Thoracic and Cardiovascular Surgery, vol. 83, No. 5, May, 1982).
G. Geary et al., "Quantitative Assessment of Infarct Size Reduction by Coronary Venous Retroperfusion in (List continued on next page.)

*Primary Examiner*—Francis Jaworski
*Assistant Examiner*—George Manuel
*Attorney, Agent, or Firm*—Trask, Britt & Rossa

[57] ABSTRACT

A retrograde perfusion system has a catheter and a driver to inject retroperfusate into the coronary sinus.

The catheter has a balloon which is inflated and deflated to first occlude and then drain the coronary sinus. During occlusion, retroperfusate is injected under pressure by the driver which also operates the balloon all in accordance with a preselected program.

51 Claims, 16 Drawing Sheets

OTHER PUBLICATIONS

Baboons" (The American Journal of Cardiology, vol. 50, Dec. 1982).

S. Meerbaum et al., "Diastolic Retroperfusion of Acutely Ischemic Myocardium" (The American Journal of Cardiology, vol. 37, Mar. 1976).

A. Berdeaux et al., "Effects of Diastolic Synchronized Retroperfusion on Regional Blood Flow in Experimental Myocardial Ischemia" (The American Journal of Cardiology, vol. 47, May, 1981).

J. Farcot et al., "Synchronized Retroperfusion of Coronary Veins for Circulatory Support of Jeopardized Ischemic Myocardium" (The American Journal of Cardiology, vol. 41, Jun. 1978).

P. Menasche, "Retrograde Coronary Sinus Perfusion: A Safe Alternative for Ensuring Cardioplegic Delivery in Aortic Valve Surgery" (The Annals of Thoracic Surgery, vol. 34, No. 6, Dec. 1982).

M. Feola and L. Wiener, "A Method of Coronary Retroperfusion for the Treatment of Acute Myocardial Ischemia" (Cardiovascular Diseases, Bulletin of the Texas Heart Institute, vol. 5, No. 3, Sep. 1978.)

R. Poirier et al., "Drip Retrograde Coronary Sinus Perfusion for Myocardial Protection During Aortic Cross-Clamping" (The Journal of Thoracic and Cardiovascular Surgery, vol. 70, No. 6, Dec. 1975).

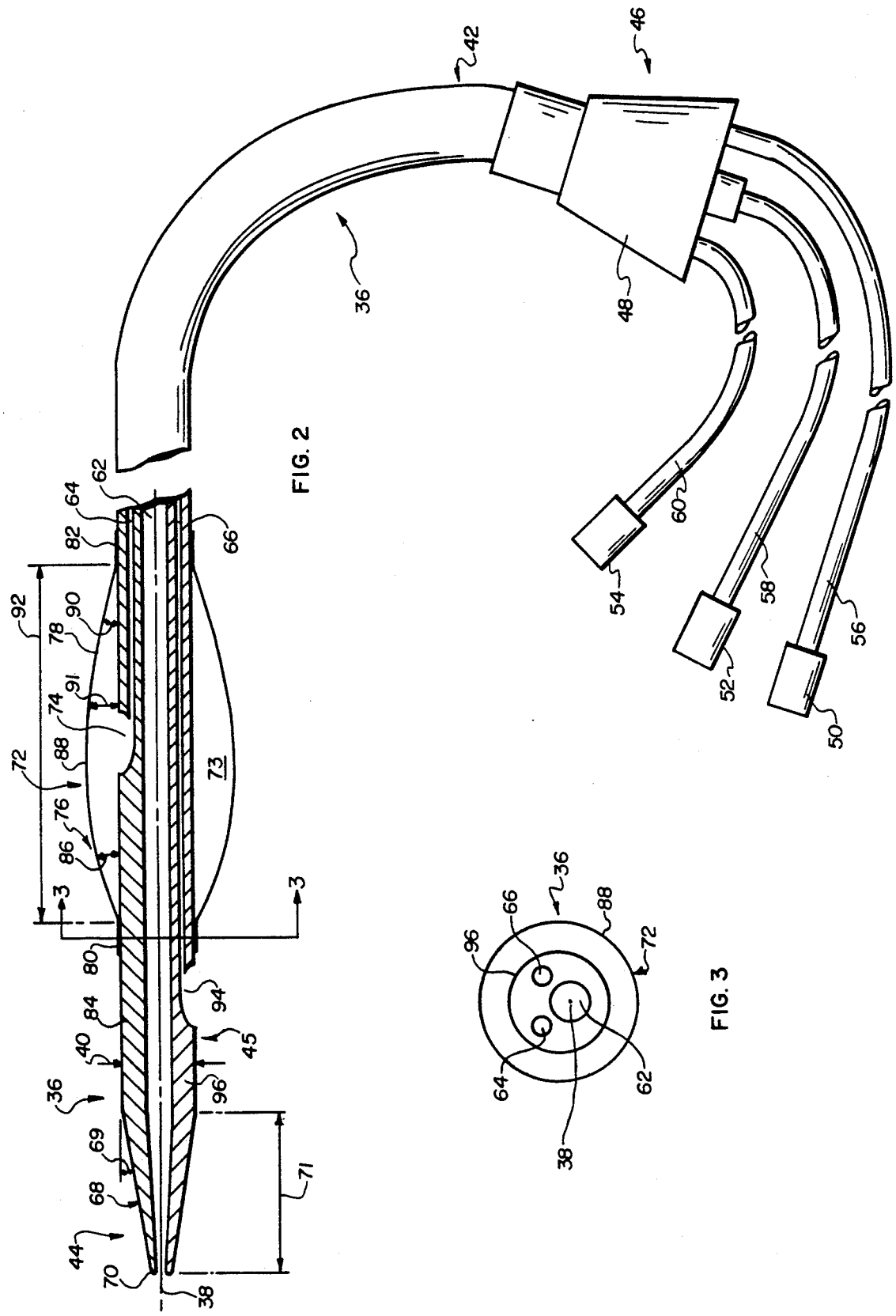

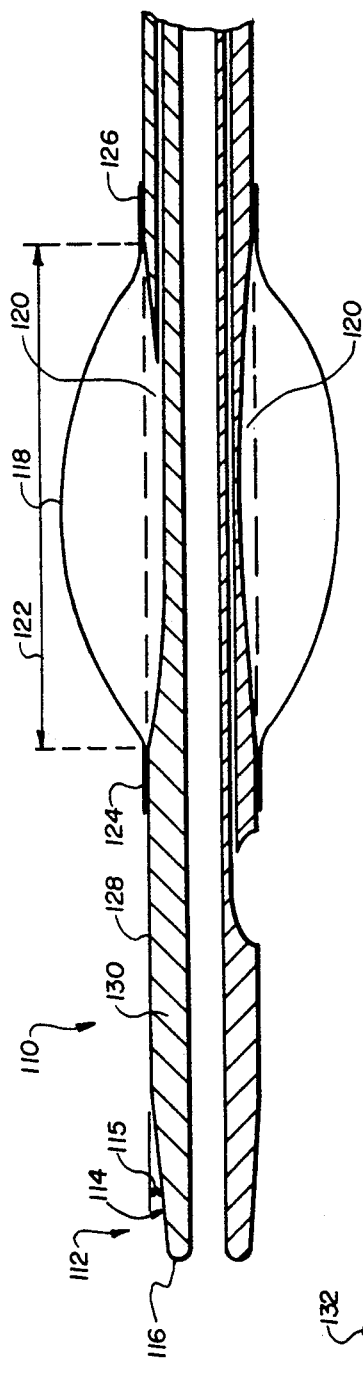
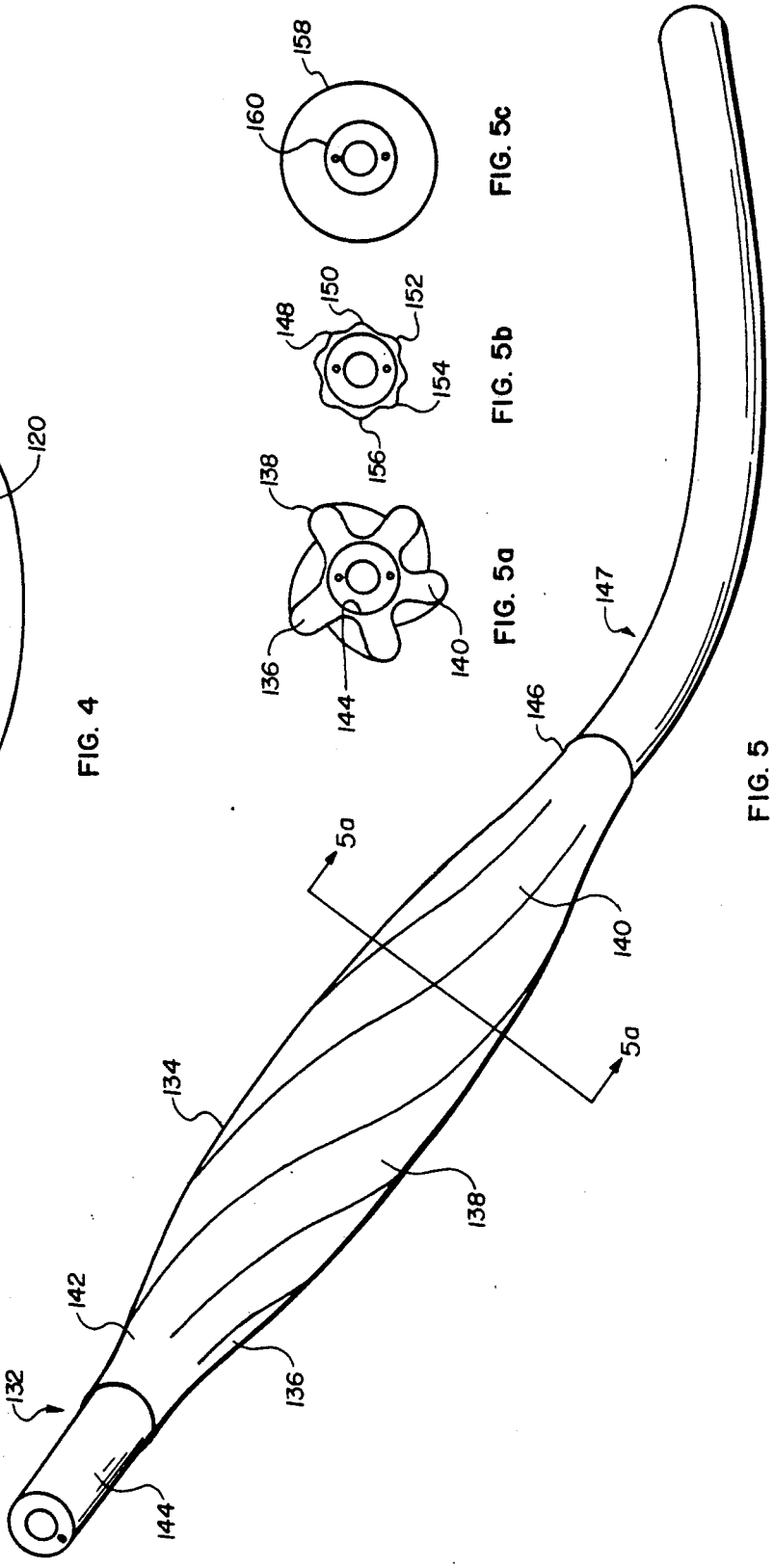

PRIMING SYSTEM LOGIC, BLOCK DIAGRAM

RETROGRADE PERFUSION SYSTEM, COMPONENTS AND METHOD

BACKGROUND OF THE INVENTION

1. Field

This invention relates to medical treatment apparatus, systems and methods. More particularly, this invention provides apparatus, systems and methods for retrograde perfusion into a lumen of the body and even more specifically, for retrovenous perfusion into the coronary sinus region.

2. State of the Art

Retrograde perfusion of fluids such as drugs and blood either separately or together has been studied for a number of years. Retrograde perfusion has been considered desirable in order to supply drugs (e.g., free radical scavengers, calcium channel drugs, antiarrhythmics such as xylocaine, tissue plasminogen activators (TPRA), streptokinease, edema reducing drugs and cardioplegia) and oxygenated blood to, for example, ischemic regions of the myocardium (heart) due to either a naturally occurring occlusion or an induced occlusion due to, for example, aortic cross clamping which is effected in order to perform some desired surgical procedure involving the myocardium.

Retrovenous perfusion into the coronary sinus while performing aortic cross clamping procedures or other similar surgical procedures typically involves some type of arrangement in which cardioplegic fluid(s) are delivered through catheters into the coronary sinus region. Since arterial flow to the myocardium is typically interrupted, the volume of retroperfusate introduced is not additive to the natural volume of venous blood exiting through the sinus region. Thus, retroperfusate is supplied under pressure to migrate in a retrograde fashion through the venous system and capillaries into the arterial system. See, e.g., R. A. Poirer, et al, *Drip Retrograde Coronary Sinus Perfusion for Myocardial Protection During Aortic Cross-Clamping*, The Journal of Thoracic and Cardiovascular Surgery, Vol. 70, Number 6, December 1975.

Retrovenous or retrograde perfusion in the coronary sinus region during a natural arterial occlusion has been suggested. Typical systems employ some type of pulsatile or synchronous delivery system to introduce retroperfusate into the myocardial sinus region. G. T. Smith, et al., *Reduction of Infarct Size by Synchronized Selective Coronary Venous Retroperfusion of Arterialized Blood*, The American Journal of Cardiology, Vol. 48, p. 1064 (December 1981). Synchronization may be effected through use of an R-wave signal obtained from a typical electrocardiogram (ECG or EKG) which is thereafter electronically processed and used to trigger (turn on and turn off) appropriate pumping structure to inject retroperfusate during diastole and to stop injection during systole. Synchronization has also been effected by monitoring venous or arterial system pressure to in turn synchronize pumping with diastole and systole. G. G. Geary, et al., *Quantitative Assessment of Infarct Size Reduction by Coronary Venous Retroperfusion in Baboons*, The American Journal of Cardiology, Vol. 50 (December 1982). S. R. Gundry, *Modification of Myocardial Ischemia in Normal and Hypertrophiced Hearts Utilizing Diastolic Retroperfusion of the Coronary Veins*, J. Thoracic & Cardiovascular Surgery, pages 659–669 (May 1982). That is, during systole (contraction of the myocardium) pumping is interrupted or stopped in order to allow blood to drain through the coronary sinus and into the vena cava. See: European Patent Application 8500326.7, filed Jan. 1, 1985 and published Aug. 7, 1985, publication number 0150960; and U.S. Pat. No. 4,459,977 (Pizon, et al.) During diastole (relaxation) pumping is initiated to introduce retroperfusate (e.g., drugs or oxygenated blood) into the sinus region under pressure sufficient to be transported in a retrograde fashion through the venous system and the capillaries in order to supply the drug and/or oxygenated blood thereto to reduce or minimize the ischemia resulting from the occlusion, and in turn, minimize the incidence and degree of necrosis and further to reduce the morbidity rate associated with myocardial infarction. See, e.g., S. Meerbaum, et al., *Hypothermic Coronary Venous Phase Retroperfusion: A Closed-chest Treatment of Acute Regional Myocardial Ischemia*, Circulation Vol. 65, No. 7, p. 1435 (June 1982).

An alternate system of a retrovenous myocardial treatment has been disclosed in which the coronary sinus is intermittently occluded to cause venous blood redistribution into ischemic regions for an unspecified period of time until a particular pressure is sensed or detected in the coronary sinus region upstream of the occlusion. The coronary sinus was thereafter opened to permit drainage and in turn a reduction of pressure in the sinus. Thereafter, the occlusion was again effected. The procedure employed a catheter with an inflatable balloon positioned within the coronary venous system. The catheter had a separate orifice or lumen to measure coronary venous pressure, W. Mohl, et al., *Reduction of Infarct Size Induced by Pressure-Controlled Intermittent Coronary Sinus Occlusion*, The American Journal of Cardiology, Vol. 53, p. 923 (Mar. 5, 1984).

Apparatus for retrovenous or retrograde perfusion, and more particularly catheters therefor, typically employ a balloon positioned proximate the proximal tip or end. The balloon is inflated in order to effect an occlusion in a lumen of the body, such as a coronary vein or the coronary sinus, so that retroperfusate may thereafter be pumped under pressure counter to the normal venous flow or normal flow in the lumen. The balloon is thereafter periodically collapsed or deflated in order to permit drainage and to avoid damage to the heart and/or venous system due to overpressure and for other purposes. See, U.S. Pat. No. 4,459,977 (Pizon, et al.) It has been reported that pressures in excess of 60 millimeters (mm) of mercury (Hg) in the coronary sinus, for example, may induce some type of pressure damage such as hemorrhage, ecchymosis or edema.

Heretofore it does not appear that the efficacy of retrovenous or retrograde perfusion is inherently effected by the amount of time and the pressure at which the retroperfusate is being urged backward counter to the flow in the particular lumen which has been occluded. Other factors, including the size of the lumen, the type of retroperfusate, the degree of normal flow such as normal arterial flow in the region to be retroperfused are also variables which have not collectively been considered to have an impact on the efficacy of the treatment. Further, it must be recognized that the venous system is naturally intended to remove undesirables including, for example metabolites, which physiologically must periodically be removed in order to maintain healthy tissue in the retroperfused region. Thus, effective and rapid drainage has not been viewed as desirable, especially to minimize the time when retroperfusion is interrupted. No structure to facilitate rapid drainage through the lumen that is occluded periodically and specifically past the balloon of a catheter introduced to perform retrograde or retrovenous perfusion is known or has been suggested. Also, no systems to maximize retrograde perfusion time under optimized but safe pressure have been suggested.

Some of the systems for retrograde perfusion disclosed heretofore have included apparatus external to the patient for supplying retroperfusate in accordance with pulsatile programs wherein the delivery schedule is synchronized to heart operation as determined through ECG signals or the periodic changes in diastolic and systolic blood pressure (e.g., U.S. Pat. No. 4,459,977). These systems do not therefore appear to maximize the retroperfusion therapy in the desired region under treatment because of what is presently believed to be insufficient migration or retroperfusion time. Apparatus which provides for extended automatic and safe operation and for practical long term retroperfusion therapy has not heretofore been available. Further, methods of retroperfusion therapy and methods for constructing certain preferred components of the retroperfusion system have heretofore not been known or available.

SUMMARY OF THE INVENTION

A catheter includes catheter means or a cannula with balloon means adapted proximate the proximal end. The balloon is operable between an inflated condition and a deflated condition. The balloon is formed and adapted to the catheter or cannula to facilitate fluid flow therepast in a lumen when in a deflated condition. The cannula includes connector means adapted to the distal end of the cannula for connection to a fluid source or reservoir. Balloon-inflating means is associated with the cannula for operating the balloon means between the inflated and deflated conditions.

The balloon means is preferably formed to have an elongated cigar-like shape with a taper toward the proximal end and also desirably towards the distal end. The taper desirably has an angle of less than about 40° as measured between the exterior surface of the catheter or cannula and the outer surface of the balloon and preferably between about 25° and about 35°. The cannula preferably has a first channel formed extending between the distal and proximal ends thereof for the communication of fluids therebetween. Preferably the balloon-inflating means includes a second channel formed in the cannula and in communication with the interior of the balloon for communicating inflation and deflation signals thereto which are preferably fluid pressure signals. The cannula also preferably includes a third channel formed therein for sensing pressure. The third channel has a port in fluid communication with the lumen into which the cannula or catheter is placed between the proximal end and the balloon means.

The cannula is also preferably formed to have a recess formed proximate the balloon means so that when the balloon means is in the deflated condition portions of the balloon means are within the recess. The balloon means is presently formed of a material which is selected to hold pressure when inflated (fluid including gas impervious) and sized to substantially occlude the lumen into which it is placed when it is in the inflated condition. The material of the balloon means is presently a substantially inelastic polyurethane material.

A retrograde perfusion driver is provided for connection to a retrograde perfusion catheter. The driver includes retroperfusate supply means which supplies retroperfusate under pressure to the retrograde perfusion catheter. The driver also has balloon operation means in communication with the retrograde perfusion catheter to generate and supply operating signals to a balloon positioned proximate the proximal end of the retrograde perfusion catheter to cause the balloon to operate between an inflated condition and a deflated condition. The driver also includes control means to generate control signals to cause the retroperfusate supply means to operate to supply the retroperfusate under pressure and control signals to cause the balloon operation means to generate and supply operating signals to the balloon, all in accordance with a preselected pattern.

The retroperfusate supply means preferably includes a pump for pumping retroperfusate. A source of retroperfusate is connected to the pump to supply retroperfusate thereto. Tube means are interconnected between the pump outlet and the retrograde perfusion catheter to supply the retroperfusate thereto. The pump is preferably a roller pump having an electrical motor connected to drive the roller pump. The control means of the driver supplies control signals which are power signals to operate the electrical motor.

The balloon operation means preferably includes an operating signal generator and actuation means connected to the operating signal generator for operation thereof. The operating signal generator is desirably a fluid pump which supplies and extracts (or aspirates) fluids for inflation and deflation of the balloon. The pump most preferably is a syringe with a plunger. The actuation means includes a member mechanically associated with the plunger for movement thereof.

In one embodiment, the actuation means desirably includes a lever pivotally mounted to rotate about an axis between an in position and an out position. An air-operated piston is connected to one end of the lever. A source of pressurized air supplies air pressure to the piston for operation of the shaft upon operation of appropriately positioned solenoid valves to port air to and away from the piston upon receipt of control signals from the control means. In another but preferred embodiment, the air-operated piston is mechanically connected to directly operate the pump and more specifically to urge the plunger of the syringe inwardly and outwardly.

The driver structure also preferably includes pressure detecting means connected to the retrograde perfusion catheter to receive pressure signals reflective of fluid pressure proximate the proximal end of the catheter. Pressure signals are sent to the control means to receive the pressure signal and compare them with preselected values and to in turn cause the control signals to be generated to operate the actuation means.

The pressure detecting means of the driver also preferably includes a flush system. The flush system includes a source of flush fluid under pressure which is connected to supply a continuous flow of flushing fluids through the pressure detecting means and through a second channel of the catheter or cannula which second channel is in fluid communication with the lumen between the balloon and the proximal end of the cannula to sense pressure in the corporeal lumen.

The driver also preferably includes a priming system connected to the actuation means. The priming system intermittently or selectively operates first to extract substantially all fluid from the balloon and the fluid pump and in sequence to supply a metered amount of selected fluid thereto. The fluid is desirably a gas, and more particularly, a gas of the class which is readily absorbed in the blood to minimize the risk of embolism, such as helium.

The retrovenous perfusion system particularly includes a catheter of the type hereinbefore described sized and dimensioned to be positioned through a vein and into a lumen in the coronary sinus region of the heart. A driver of the type hereinbefore described is interconnected to the catheter for supplying retroperfusate thereto and for operating the balloon in accordance with preselected patterns. A method of manufacturing the catheter and a method of performing retroperfusion therapy is also set forth.

BRIEF DESCRIPTION OF THE DRAWINGS

In the drawings, which illustrate the best mode presently contemplated for carrying out the invention.

FIG. 2 is a cross-sectional view of portions of a catheter of the instant invention along the longitudinal axis thereof;

FIG. 3 is a cross-sectional view of the catheter of FIG. 2 along section lines 3—3;

FIG. 4 is a cross-sectional view along the longitudinal axis of a catheter of the instant invention;

FIG. 5 is a perspective view of a portion of a catheter of the instant invention;

FIGS. 5A, 5B and 5C are cross-sectional views of alternate embodiments of the structure shown in FIG. 5;

FIG. 6 is a simplified representation of an alternate embodiment of a component of the driver shown in FIG. 6;

DESCRIPTION OF THE ILLUSTRATED EMBODIMENT

The illustrated embodiment hereinafter described in more detail is described specifically for retrovenous perfusion of the coronary sinus region. It should be particularly understood, however, that retrograde perfusion may be an available therapy for other organs and for other regions of a body in which it is desired to periodically urge fluids in a direction counter to their normal direction of flow within a corporeal lumen.

Figure 1:
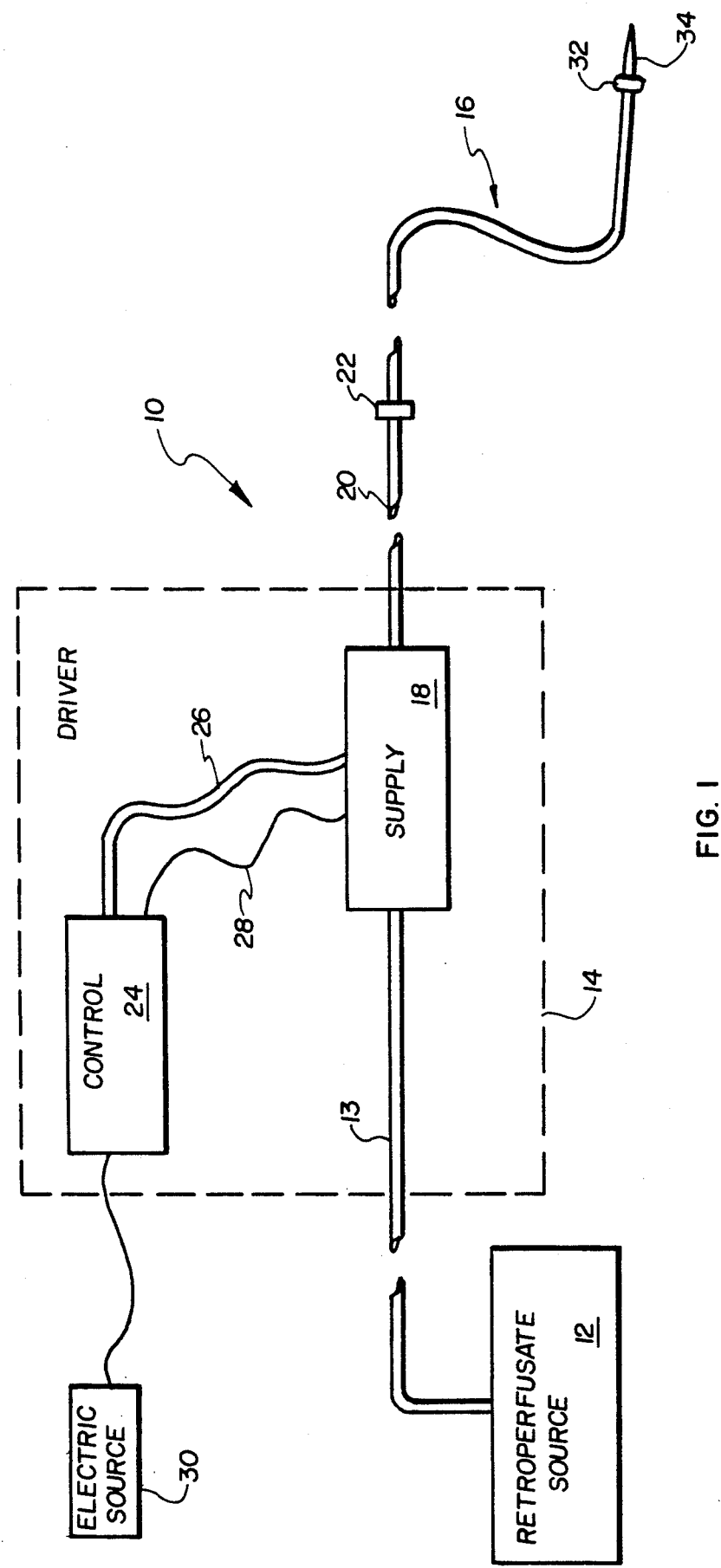
FIG. 1 is a simplified block diagram of the components of a retrovenous perfusion system of the instant invention.

Referring now specifically to FIG. 1, a simplified block diagram of a retrograde perfusion system, generally indicated by the numeral 10, includes a source of retroperfusate 12 interconnected to a driver 14 and to a retrograde perfusion catheter 16. The source 12 supplies retroperfusate, such as oxygenated blood, therapeutic drugs, such as solutions containing bicarbonate or other desired drugs, or combinations of blood and drugs to a supply structure 18, which receives the retroperfusate and supplies it under pressure via tubing 20 and connector 22 to the retrograde perfusion catheter 16. As shown, the driver 14 includes a control 24 which functions as a control means to supply control signals to the supply structure 18 via associated interconnecting tube means 26 and conductor means 28, all of which is discussed in more detail hereinafter. The control 24 is also shown to receive electrical energy from a source 30, which is typically a source of external electrical power, such as 115 volt power from a wall outlet.

It should be noted that the retrograde perfusion catheter 16 has a balloon 32 positioned proximate the proximal end 34 which balloon is also operated by the supply structure 18 via control signals received from the control 24. The control signals cause the retroperfusate to be supplied and the balloon to be periodically operated (between inflated and deflated conditions) in accordance with a program of retroperfusion therapy selected by the user, as more fully discussed hereinafter.

Retroperfusion Catheter

A desired retroperfusion catheter is generally shown by the number 36 in FIG. 2. A cross section thereof along the axis 38 is depicted in FIG. 3. The catheter in FIGS. 2 and 3 is shown considerably larger than the actual size for purposes of illustration. In reality, the catheter 36 is sized to fit within selected lumens of the body. More particularly, in the embodiments here described and illustrated, it is sized for insertion through the venous system from a point external the body into a selected vein of the coronary sinus region. The catheter is preferably generally round in cross section and has a diameter 40 from about 1½ to about 3 millimeters.

The catheter 36 shown in FIGS. 2 and 3 has a proximal end 42 and a distal end 44. The proximal end 42 has connection means 46 associated therewith for connection to an external driver or other apparatus, as more fully described hereinafter. The particular connection means 46 here illustrated includes a cuff structure 48 which provides for interconnection of individual or separate connectors 50, 52 and 54 through associated tubing 56, 58 and 60 to the first channel 62, the second channel 64 and the third channel 66 formed in the illustrated portion of the catheter 36 between the ends 42 and 44 which function as cannula means. That is, the connectors 50, 52 and 54 provide for connection to external means for fluid intercommunication with their respective channels 62, 64 and 66. Of course, it should be understood that the cannula means is sized in length so that the connecting structure or cuff 46, including the individual connectors 50, 52 and 54 are external to the body when the distal end 44 is positioned in the desired location in the desired corporeal lumen. That is, the overall length of the catheter 36 along its axis 38 is selected to extend, for example, from the coronary sinus region through the various selected lumens of the body to exterior the body for interconnection to appropriate external structure, as more fully discussed hereinafter.

As can be seen from FIG. 2, the catheter 36 has a first channel 62 formed therein which is in fluid communication between the distal end 44 and the proximal end 42 for the communication of fluids therebetween. That is, in some circumstances, it may be desirable to extract fluids with a catheter of this particular type as well as to supply fluids such as a retroperfusate. However, in the specific embodiments herein described, channel 62 is for the transmission of retroperfusate from external to internal the body.

The catheter 36 is preferably formed of a plastic-like material selected so that the end portion 45 (e.g., the about 7 to about 11 centimeter portion from the tip 70 at the distal end 44 toward the proximal end 42) is stiff enough to be manipulable, but soft enough so that it does not penetrate or damage any lumen through which it is to be passed, or against which pressure is exerted through a course of threading the catheter 36 into the particular desired region of the body. For example, positioning the catheter 36 into the coronary sinus is readily recognized to be delicate. Damage to the various intermediate veins is to be avoided by use of a flexible, yet firm, structure. Flexibility, of course, is needed to minimize damage to the veins, while firmness is needed to facilitate manipulation past the various venous junctions as the catheter 36 is inserted and to hold the catheter in place specially when the balloon is inflated. That is, the pressure in the retroperfused region acts to urge the catheter downstream. A selected level of firmness in the catheter or cannula material reduces the tendency of the distal end to slide downstream. Presently, a material of about 60 to about 68 durometer on the "D" scale has been found to be particularly suitable.

Referring specifically to FIG. 2, it can be seen that the tip proximate the distal end 44 has a tapering portion 68 to facilitate threading of the catheter 36 into the desired region of the body. The very end or tip 70 of the cannula has rounded edges to preclude scratching the lumen through which it is being inserted and to minimize friction to facilitate ease of insertion. The degree of taper 69 of the tapered portion 68 may be varied by the user. In the embodiment here illustrated, the tapered portion 68 extends from the tip 70 toward the distal end 44 a distance 71 of approximately 5 centimeters.

The balloon means here in the form of a balloon 72 is positioned about the catheter 36 proximate the distal end 44. Means to operate the balloon 72 between an inflated condition and a deflated condition is here shown as a second channel 64 formed in the catheter or cannula 36 to communicate inflation signals and deflation signals which are extracted here and selected to be fluids and more particularly fluid pressure signals sent to and from the balloon 72 through a port 74. The fluids, of course, are transmitted via the channel 64 and the connector 50 from an external source.

The balloon means 32 (FIG. 1) is formed and adapted to the catheter 16 (FIG. 1) to facilitate fluid flow therepast. For example, the balloon 72 of catheter or cannula 36 is constructed to have a preselected pressure drop of less than about 6 mm Hg with fluid flowing in the corporeal lumen such as a vein (e.g., about 4 to 6 millimeters effective or mean diameter) in the coronary sinus region when the balloon 72 is in the deflated condition. Desirably, the pressure drop across the balloon 72 in the deflated condition will be less than 4 mm Hg and most preferably less than about 2 mm Hg. For larger lumens or veins, a proportionally larger catheter 16 and balloon means 32 will be used and a proportionally larger pressure drop may be acceptable.

The balloon 72 is shown in FIG. 2 in an inflated condition. It is cylindrical with the cannula 36 passing axially therethrough and is formed to have what may be deemed to be a cigar-like shape with a portion 76 tapering towards the distal end 44 and another portion 78 tapering towards the proximal end 42. Portions 80 and 82 are secured to the outer surface 84 of the catheter 36 in a conventional manner such as by a suitable adhesive or by other appropriate means.

In the inflated condition, it can be seen that the tapering section 76 of the balloon 72 tapers towards the proximal end at an angle 86, which is here shown to be about 30°. The angle 86 is measured between the outer or exterior surface 84 of the catheter or cannula 36 and the outer or exterior surface 88 of the balloon 72 in the inflated condition. This angle 86 may be selected to be from about 40° to about 20° and is desirably between about 25° and about 35° and most preferably about 30°. The angle 90 of the balloon 72 as determined between the exterior surface 84 of the catheter 36 and the outer surface 88 of the balloon 72 towards the proximal end 42 of the catheter 36 is formed to be substantially identical to the distal end angle 86. The angles 86 and 90 are selected based on empirical tests so that in the deflated condition, the balloon 72 presents a small cross section to fluid flowing in the lumen into which the catheter 36 is positioned. That is, the smaller the cross section, the less resistance the catheter or cannula 36 with balloon 72 will present to fluid flow therepast. Indeed, a low profile is presented. A smaller angle 86 and 90 (e.g., less than about 20°) is not desirable because the balloon 72 then becomes of insufficient inflated height 91 or cross section absent unacceptable length 92 when fully inflated to properly occlude a lumen into which the catheter 36 is placed. That is, a balloon which is elongated due to selection of an angle less than 20° provides increased surface area for fluid migration therethrough, presents an extended distance of fluid resistance undesirably increasing the pressure drop thereacross and may block fluid flow in the lumen which preferably should not be blocked. This is particularly so for a catheter 36 with the dimensions heretofore specified in the coronary sinus region. For a balloon 72 with angles 86 and 90 selected at about 30° is sized to have a length 92 of from about 8 to about 12 millimeters.

It should further be noted that the balloon 72 is constructed of a substantially inelastic, preferably polyurethane-type, material approximately 2 to 4 mils in thickness. The material selected should be substantially resistant to migration or essentially non-porous to liquid and more particularly to gases which may be used to inflate the balloon. Presently available elastic-type materials have been found to be unsatisfactory because of their higher porosity, thus allowing for gradual deflation after inflation. That is, the fluids (e.g., gases) used for inflation leak or migrate through the balloon itself so that the pressure in the balloon for inflation cannot be maintained over time and thus the presence of fluids in the lumen upstream of the distal end 44 of the catheter 36 cannot be maintained, as desired. Further, present elastic-type materials have been found to lack durability for repeated inflation and deflation. They simply wear out too fast and even though they are desirable because they collapse snugly about the cannula 36 in the deflated condition to present a lower profile and a lower pressure drop to fluids flowing in the lumen.

It can also be seen in FIG. 2 that a third channel 66 is formed in the catheter 36 to be in communication with a second port 94 which is in fluid communication with the interior of the lumen. Fluid pressure in the lumen proximate and upstream of the occlusive or inflated balloon 72 can be communicated through the channel 66 and through connector 54 to exterior of the patient. It should be recognized, however, that the pressure sensing means associated with the catheter 36, such as the channel 66 in combination with the sensing port 94, is but one alternative available for sensing pressure between the balloon 72 and the distal end 44 of the catheter 36. A microelectronic transducer may be suitable in some applications for installation in the vicinity of the port 94 and an appropriate electrical conductor formed in the sidewall 96 of the cannula 36 or even positioned within the channel 62 desired to transmit pressure signals to exterior the patient.

FIG. 3 shows catheter 36 in cross section normal to the longitudinal axis 38 at section lines 3—3 of FIG. 2. The balloon 72 is shown in a substantially inflated condition.

Referring now to FIG. 4, a partial cross-sectional view similar to FIG. 2 of an alternate embodiment of a catheter or cannula 110 is depicted. The catheter or cannula 110 is sized substantially the same as the catheter 36 described in FIG. 3. The proximal end 112 is formed without a substantial taper portion. That is, the end portion 114 tapers 115 somewhat towards the tip 116, but not to the same degree as in FIG. 2. Indeed, it has been found that no taper is really necessary as long as the tip 116 is formed with rounded edges to preclude damage to the interior of the corporeal lumens and to minimize friction to facilitate insertion into and through corporeal lumens. The balloon 118 of the catheter 110, shown in FIG. 4, is formed in substantially the same way as the balloon 72 of FIG. 2.

It should be noted that the catheter 110 of FIG. 4 has a recess 120 formed therein proximate the balloon 118. The recess 120 is sized in length 122 substantially the length of the balloon 118 in the inflated or deflated condition except for those portions 124 and 126 of the balloon 118 which are sized for securement to the outer surface 128 of the catheter 110. The recess 120 may be formed in the catheter 110 by any acceptable means, including heat stretching, extrusion, grinding or buffing. The recess 120 is formed into the sidewall 130 of the catheter or cannula 110 in order to provide additional space for the balloon 118 to reside when in the collapsed condition. This recess 120, therefore, facilitates reduction of the profile or the effective cross section of the balloon 118 in the deflated condition because portions of the balloon 118 are forced therein by fluid pressure in the lumen. The resistance to fluid flow imposed by the catheter 110 and balloon structure 118 when placed in a fluid transporting and carrying lumen is thereby reduced.

It should be noted that prior art balloons have not heretofore been sized or shaped to present a reduced or low resistance to fluid flow therepast. It has been noted, for example, that a conventionally structured balloon positioned in the lumen of, for example, the coronary sinus region, experiences a pressure drop thereacross of approximately in excess of 8 to 10 mm Hg. With the balloon shaped and sized as described in FIGS. 2 and 3, the pressure drop has been measured for blood flow to be approximately 2 mm Hg. With the addition of the recess 120, as described in FIG. 4, an additional reduction in pressure drop is expected because the effective cross section in the fluid flow path will be further reduced.

Referring now to FIG. 5, a partial perspective view of an alternate embodiment of the balloon means of a catheter 16 is depicted. In particular, the catheter 132 has a balloon 134 adapted thereto proximate the proximal end. The balloon 134 is formed to have a plurality of ribs when in the deflated condition. As here shown, three ribs 136, 138 and 140 are formed by securing one end 142 of the balloon 134 to the outer wall 144 of the catheter 132. The balloon 134 in the deflated condition is then twisted or rotated to create a series of ribs and then secured at its other end 146. Securement may be by adhesive or other conventional means.

FIG. 5A is a cross section at section lines 5A of the catheter of FIG. 5 showing the respective ribs 136, 138 and 140, which are positioned approximately at 120° segments about the exterior surface 144 of the catheter 132. FIG. 5B shows a catheter similar to catheter 132 in cross section similar to FIG. 5A but with the balloon 148 collapsed tightly thereabout. In this arrangement, the ribs may collapse into a plurality of tightly formed smaller ribs, such as ribs 150, 152, 154 and 156. FIG. 5C is a cross section of a catheter similar to catheter 132 of FIG. 5 with the balloon 158 of catheter 160 in the inflated condition.

The Driver

Figure 6:
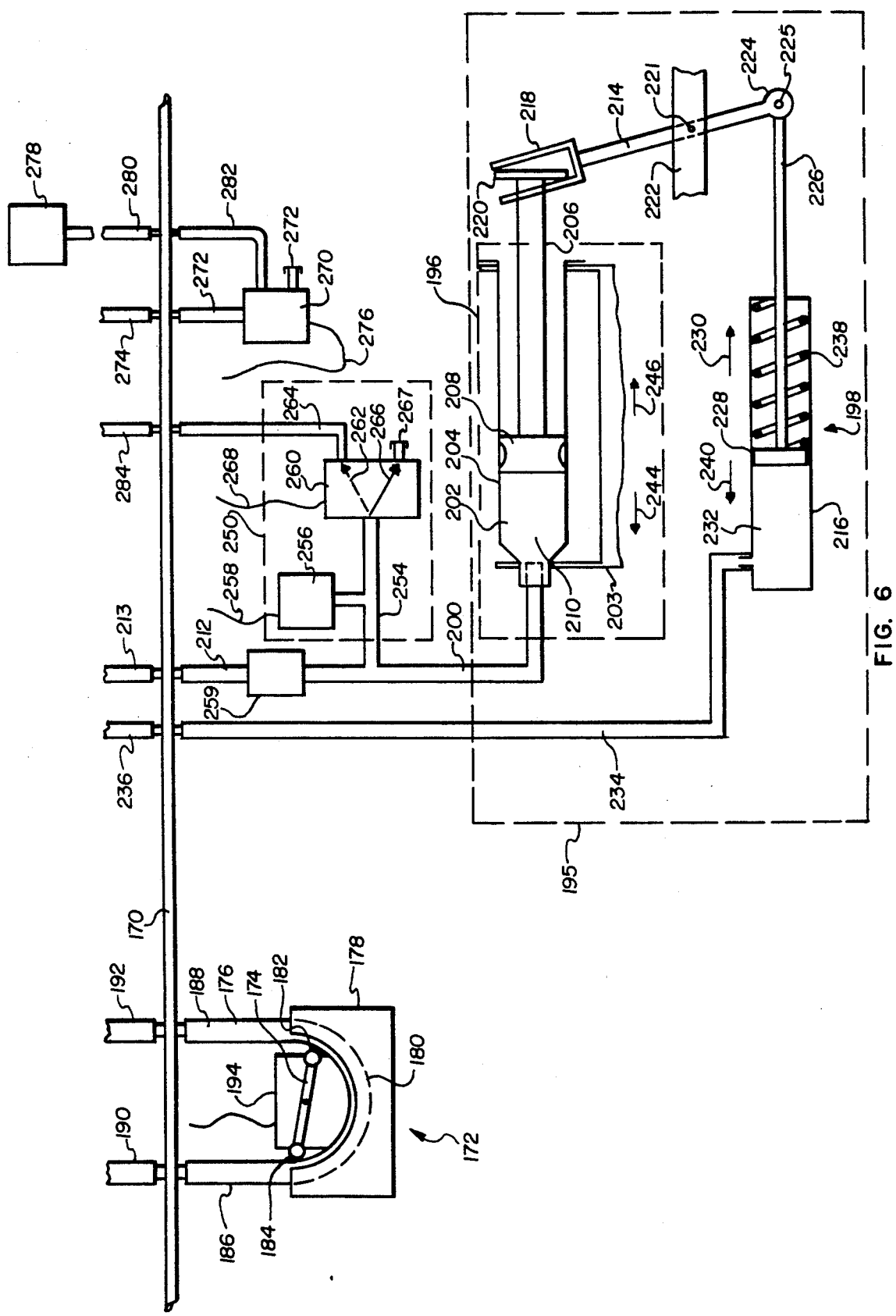
FIG. 6 is a simplified block diagram of portions of the driver for the system of the instant invention.
Figure 7:
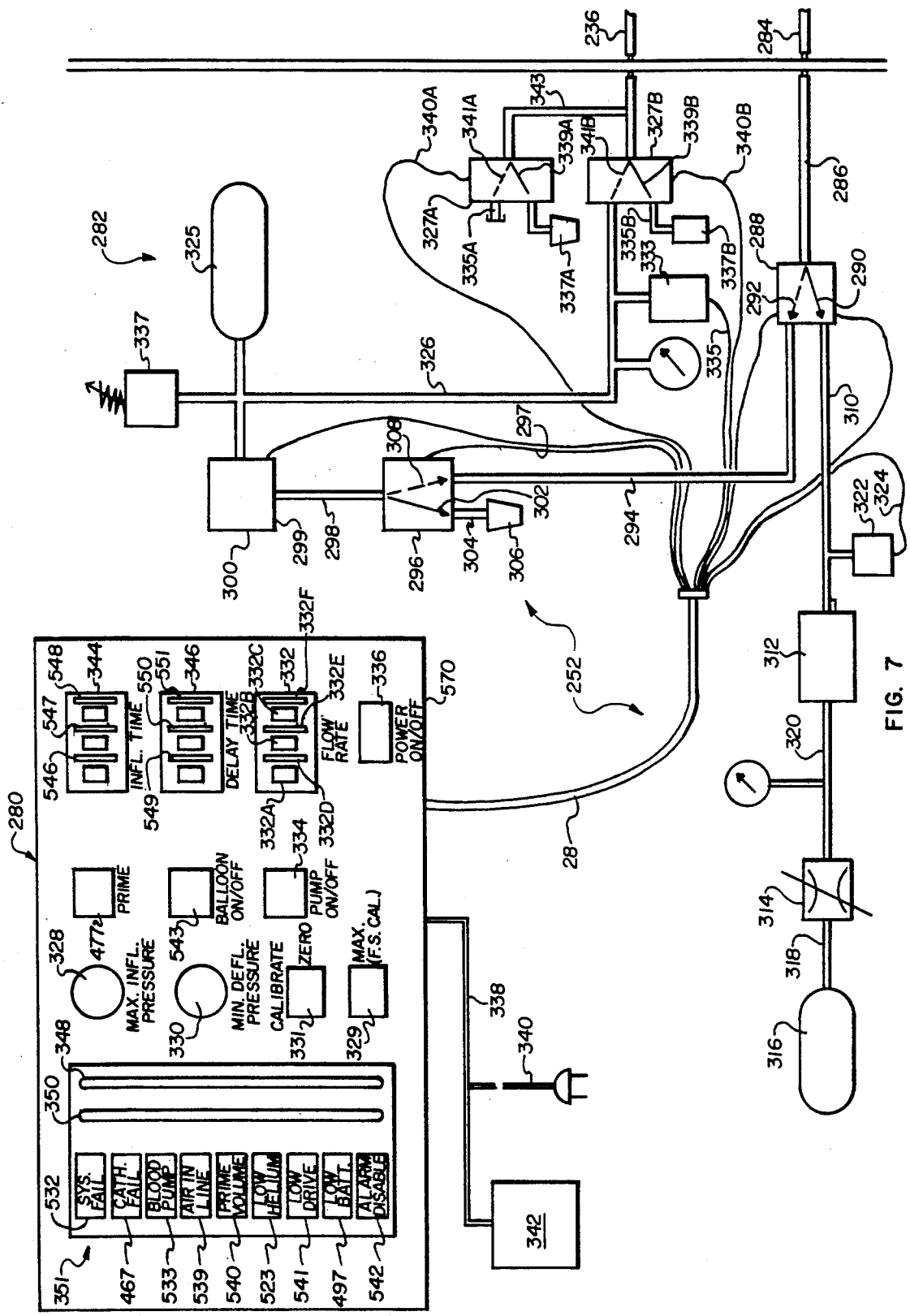
FIG. 7 is a simplified block diagram and representation of additional portions of the driver of the instant invention.

FIGS. 6 and 7 together show the various components of the driver 14 in simplified form. In general, the supply structure 18 (FIG. 1) is shown in FIG. 6 and the control 24 structure is shown in FIG. 7. Desirably, the supply structure shown in FIG. 6 is separately mounted on or in a chassis, a part of which is shown as item 170, for positioning proximate the patient. More specifically, for myocardial retroperfusion therapy, the placement of the entire driver 14 (FIG. 1) structure in the immediate vicinity of the patient may interfere with the performance of necessary medical procedures and also interfere with proper monitoring of the patient undergoing the therapy. Therefore, the supply structure 18 (FIG. 1) is positioned on a relatively small chassis for positioning immediately proximate the patient by suspension from, for example, an IV bottle hanger proximate the bed or other surface upon which the patient is positioned. The remaining structure, including specifically the control structure 24 (FIG. 1) such as the control means 280 seen in FIG. 7, may be connected thereto through tubes 26 and interconnecting conductors 28 to be positioned in another part of the room sufficiently close to be operated by attending medical personnel, yet sufficiently distant to not interfere with physical movement in and about the vicinity of the patient.

It should also be noted that the arrangement noted in the preceding paragraph is particularly preferred for myocardial retrovenous perfusion when the source of retroperfusate is selected to be blood from the arterial network of the patient. If, for example, blood is obtained from the femoral artery of the patient, the tubing, such as tubing 13 in FIG. 1, may be maintained at a relatively short length to interconnect with the supply 18 structure. Further, the tubing such as tubing 20, interconnecting from the supply structure 18 shown in FIG. 1 for connection through connector 22 to the retrograde or retrovenous catheter 16 is further kept at a minimum distance. The shorter distances or lengths are desired in order to minimize pressure drop which may be experienced as the retroperfusate passes through the tubing and further to minimize the amount of stress or damage that may be imposed on the blood by processing it in the manner herein disclosed for purposes of therapy. That is, the sheer stresses that retroperfusate, such as blood, experiences can be damaging to the blood and in particular to the red blood cells thereof reducing the efficacy of the retroperfusion therapy when its purpose is to provide, for example, oxygenated blood to an ischemic region of the myocardium.

Referring now specifically to FIG. 6, the supply 18 (FIG. 1) structure therein illustrated includes specifically pump means which is generally depicted by the number 172. The pump means here functions to supply retroperfusate to the catheter 16 (FIG. 1) under pressure. It is here shown specifically as roller pump structure 174 in association with a tube 176 positioned in a block 178 having a hemispherical groove formed therein as depicted by the dotted lines 180. The rollers 182 and 184 of the pump 174 contact the tubing 176 and squeeze it in a conventional manner to cause fluids therein to be pumped from an inlet 186 to an outlet 188. As here depicted, the fluids are received from a source or may be supplied from a reservoir from tubing 190 through an optimal connection 191. For myocardial retrovenous perfusion, the retroperfusate is preferably a source of oxygenated blood which is received via connector 191 and supply line 190 through the inlet 186. It is thereafter pumped by the roller pump 174 and supplied via the outlet 188 through lines 192 for further interconnection to a retrovenous catheter such as the one shown in FIG. 2, and more particularly to connector 52 via intermediate tubing (not shown).

The source of oxygenated blood may be the arterial system of the patient and more particularly a femoral artery. Alternately, venous blood may be extracted from another lumen or a sheath associated with the catheter 16 (FIG. 1) and its placement. The venous blood may thereafter be processed through a conventional blood oxygenator and supplied to the pump 172 via tubing 190.

Alternate pump means 172 may be used. As presently envisioned, a roller pump with rollers similar to rollers 182 and 184 are articulated and urged against associated tubing by springs to minimize wear on the preferred thin wall tubing to be used to avoid excessive wear of the tubing while maintaining acceptable pump output.

The roller pump 174 is here shown to be operated or driven by an electric motor 194 which is desirably a stepper motor. A motor manufactured by Hurst Motors of Princeton, Ind., model no. 3208-009 has been found suitable. The rate of pumping is dictated by the rate of electrical pulses delivered to the motor from the control means, as more fully discussed hereinafter.

The supply structure 18 of FIG. 1, detailed in FIG. 6, further includes balloon operation means generally depicted by the number 195. The balloon operation means 195 includes an operating signal generator, generally depicted by the number 196, and actuation means, generally depicted by the number 198.

The operating or operation signal generator 196 is any means which can supply an operating signal to cause the balloon, such as balloon 32 or 72 (FIGS. 1 and 2), to operate between their inflated and deflated conditions. The operating signal is desirably a pressure signal transmitted by a fluid, including specifically, gas. The signal is supplied via interconnecting tubing 200 to, for example, connector 50 of the catheter 36 depicted in FIG. 2. The operating signal generator 196 shown in FIG. 6 is specifically here shown to be a conventional medical syringe 202 mounted by a bracket 203 to the chassis. It acts as a pump to pump or supply the operating signal (pressure) to the balloon (e.g., 72, FIG. 2) of a catheter 36 (FIG. 2) and as an aspirator to extract fluid therefrom (lower pressure) as a deflation signal.

The syringe or pump 202 has a substantially cylindrical shape with an external wall 204. A plunger 206 moves a slidable, but snugly fitted, piston 208 in order to pump fluids out of and aspirate fluids into the chamber 210. Of course, the fluids are therefor supplied to and removed from the balloon via interconnecting tubing 200, 212 and 213.

The actuation structure 198 is here depicted to include a lever 214 interconnected to an air actuated piston 216. The lever 214 has a fork or yoke 218 here specifically shown to accommodate or receive the actuation surface 220 of the plunger 206. The yoke 218 is interconnected to the lever 214, which is mounted to pivot about a pivot pin 221 journaled in structure 222. The structure 222 and bracket 203 are here shown in break-away to indicate that both can be mounted to any associated part of the chassis sufficient to provide rigidity for operation. The opposite end 224 of the lever 214 is pivotally connected on pivot pin 225 to the shaft 226 of the air operated piston 216. The shaft 226 has a slidable, yet sealable, piston 228 which is operated in one direction 230 by air pressure which is inserted into the chamber 232 through interconnecting tubing 234 and 236. The air is supplied from appropriate structure (hereinafter described) in the control structure 24 (FIG. 1). When air pressure is removed from the chamber 232 via interconnecting tubing 234 and 236, a spring 238 positioned within the air actuated piston 216 causes the piston 222 to move in the direction 240. Thus, it can be seen that the plunger 206 can thereby be moved in an inward direction 244 and in an outward direction 246 by movement of the lever member 214 upon actuation of the air actuated piston 216.

The fluid actually being supplied to inflate and deflate the balloon, such as the balloon 72 of the catheter 36 of FIG. 2, may be air. However, air is not the most desirable fluid since any defect in the balloon could present the risk of introducing air into the blood with the associated threat of an embolism. It is here preferred to use helium, which may be more readily dissolved in the blood and reduce the risk of embolism. Further, the molecular weight of helium has been found to provide for desirable faster response times in operation.

In the present structure herein disclosed, helium may be inserted into the tubing 200, 212 and 213 and the chamber 210 of the signal generator 196 through a priming system, portions of which are shown in FIG. 6 and generally depicted by the number 250. Other portions are shown in FIG. 7 and are generally depicted by the number 252. The portions 250 shown in FIG. 6 include tubing 254 which is interconnected with tubing 200 and 212, and in turn with the chamber 210. It is also connected to the catheter, such as catheter 36 in FIG. 2, via tubing 212. In turn, tubing 254 is in communication through connector 50 to the channel 64 and the interior 73 of the balloon 72.

The tubing 254 has interconnected therein a first pressure transducer 256 to sense the pressure in the tubing 254 and in turn the tubing 213, 212 and 200, and in turn via connector 50 and channel 64 in the balloon 72. A signal reflective of the sensed pressure is transmitted via conductor 258 to the control structure 24 (FIG. 1) as more fully discussed hereinafter.

A filter 259 is optionally, but preferably, included between the priming system 250 and balloon operation means 195 and the balloon means 32 (FIG. 1). The filter 259 acts to protect the priming system and balloon operation means 195 from contamination with blood in the event of a catastrophic failure of the balloon means and transmission of blood into the tubing 212. The filter 259 may be selected to be any conventional filter which inhibits fluid flow but permits gas flow.

The tubing 254 is connected to a solenoid valve 260. The solenoid valve 260 is a conventional two position solenoid valve here simply depicted to operate between a first position shown by dotted line 262 and a second normal position shown by solid line 266. In the first position 262, an interconnection is made between helium supply line 264 and tubing 254, which is further interconnected as hereinbefore described. In the second position 266, the solenoid valve 260 is positioned to be closed or connected to a locked vent 267. The solenoid valve 260 receives operating signals via conductor 268 from the control structure 24 (FIG. 1), as more fully discussed hereinafter.

The supply structure 18 here shown also preferably includes pressure sensing means which is here shown to be second pressure detector 270 which is interconnected to tubing 272 and 274 to the catheter in use. The catheter is, for example, the catheter 36 of FIG. 2. Tubing 274 is interconnected through connector 54 to the third channel 66 and port 94 to sense the pressure in the lumen proximate the distal end 44 upstream of the balloon 72. A pressure reflective signal is transmitted via conductor 276 to the control 24 (FIG. 1) for processing, as more fully discussed hereinafter.

It should be understood that for retrograde perfusion of blood, the presence of blood at the port 94 and in the third channel 66 has been found to be generally unacceptable because of the tendency of the blood to coagulate or clot, thereby impeding transmission of pressure signals. Accordingly, a flushing system is desirable to supply a flushing fluid either intermittently or continuously through the transducer 270 and interconnecting tubing 274, 272 and through the connector 54 through the third channel 66 and out the port 94. The flushing system here preferably includes simply a source of intervenous fluid (IV) desired by the user. The IV fluid is supplied via interconnecting tubing 280 and 282 to transducer 270 under pressure obtained by elevation of the source 278 to an appropriate height. The IV fluid source 278 typically has a regulator so that the fluid flow may be regulated to be either intermittent or continuous. It is presently preferred that a saline solution with an anticoagulant (e.g., heparin) be used as the IV fluid and supplied at the rate of approximately 1 to 3 cubic centimeters (cc's) per hour to continuously flush the transducer and the interconnecting tubing 272, 274, as well as tubing 60 and channel 66.

The transducer 270 here also is shown to have a calibration port 272 for calibration upon initialization of the system or thereafter should there be any question as to whether or not the transducer 270 is transmitting appropriate or accurate signals.

Calibration may here be effected by first connecting to the port 272 tubing associated with a calibration device which may be a conventional manometer type blood pressure monitoring apparatus. That is, one form of conventional blood pressure measuring apparatus includes a manometer with associated tubing which may be readily rearranged and connected to the calibration port 272. Thereafter, an appropriate pressure can be placed in the tubing and measured precisely on the associated manometer in order to calibrate, for example, a high pressure set point for the transducer 270 which is set in a conventional manner. Thereafter, the transducer could be opened to atmosphere in order to set a low point at existing atmospheric pressure in a conventional manner.

Figure 6A:
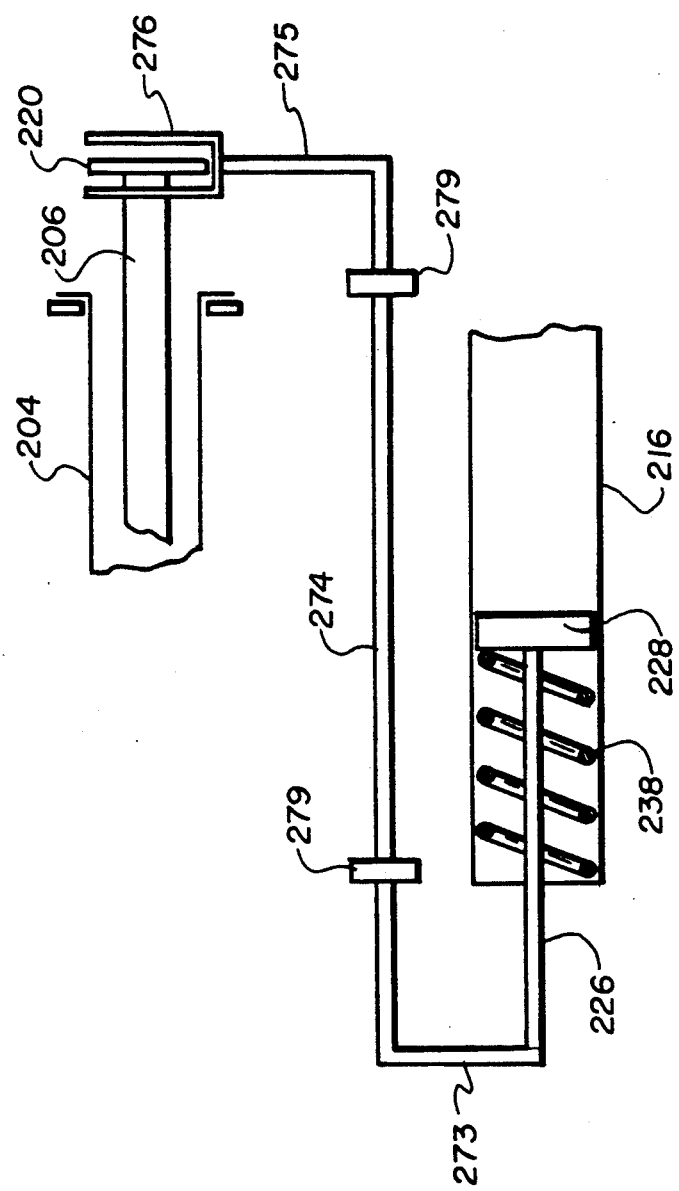

Referring to FIG. 6A, an alternate and presently preferred embodiment of the balloon operation means 195 is shown with a medical syringe 204 and air actuated piston 216 both identical to those shown in FIG. 6 but arranged differently. The shaft 226 of the piston 216 is connected to a transverse member 273 which is in turn connected to a rod 274 and another member 275 as shown. A yoke 276 is affixed to the end of the member 275 to the actuation surface 220 of the plunger 206. Two or more intermediate bushings or guides 278 and 279 are attached to the chassis to provide for stable movement of the rod 274. Thus, direct movement of the piston 228 by air or spring 238 pressure is translated into movement of the plunger 206. The arrangement, as shown, is selected to facilitate construction of a smaller and more compact supply 18 (FIG. 1) apparatus.

Referring now to FIG. 7, the control 24 (FIG. 1) structure is shown to here constitute control means 280. Also shown are parts of the priming structure 252 and of the actuation means 282 for operating the air actuator structure 198 (FIG. 6).

Referring specifically to the priming structure 252, tubing 284 interconnects between structure in FIG. 6 and tubing 286 which further connects to the priming and supply solenoid valve 288. The priming and supply solenoid valve 288 is here shown in simplified form to be operable between two positions. In the first normal position 290, the valve 288 is connected to a helium supply circuit to receive helium therefrom and to supply it through interconnecting tubing 286, 284 and 264 and through solenoid 260, as hereinbefore described. In the second position 292, the valve 288 is connected via interconnecting tubing 294 to a priming valve 296 and then through interconnecting tubing 298 to a source of vacuum which is here shown to be compressor 300. In its normal position shown in solid 302, the priming valve 296 is connected through interconnecting tubing 304 to an air filter 306 which is open to the atmosphere.

In its prime position shown by the dotted line 308, the priming valve 296 interconnects tubing 294 with tubing 298 and to the suction side or inlet 299 of the compressor 300. The priming valve is controlled by signals received from the control means 280 via conductor 297. Thus, upon activation of the compressor 300, a suction or vacuum or negative pressure is transmitted through line 298 and via valve 296 and then through line 294 and valve 288. In turn, the negative pressure is transmitted through interconnecting tubing to the chamber 210 (FIG. 6) and to the balloon of the connected catheter. The negative pressure evacuates or draws a vacuum to remove all gas therein including blood gases which have migrated into the tubing through the balloon.

Referring back to the priming and supply valve 288, when the valve is in the normal position 290, it is interconnected through tubing 310, a pressure regulator 312 and a bleed valve 314 to a helium source 316 via tubing 318 and 320. In operation, helium from the source 316 is supplied through a bleed valve 314 to a pressure regulator 312, which is set to ensure that excessive pressures are not transmitted. Thereafter, the helium is supplied through the valve 288 and through interconnecting tubing, as hereinbefore described. A pressure transducer 322 may be interconnected in the tubing 310 to supply pressure signals reflective of the pressure in the line 310 via conductor 324 to the control 24 structure, and more particularly the control means 280, as hereinafter described. The alarm 323 may be activated by the control means 280 when the signal reflects a low helium pressure to alert the operator that the helium supply is low or nearing exhaustion.

In operation, the priming system 250 (FIG. 6) and 252 (FIG. 7) operates periodically to first remove all fluid (e.g., helium) from a balloon, such as balloon 72 (FIG. 2), and the interconnecting channel, such as channel 64, tubing 56 and interconnecting tubing 200, 212 and 213 as well as the chamber 210. Thereafter, the system operates to back-fill it with a specific metered amount of helium determined by the presettings of the valves 312 and 314 and the time the valve 260 (FIG. 6) is held in position 262 by control signals from the control means 280.

Upon receiving an appropriate priming signal, the solenoid valve 260 (FIG. 6) shifts from its normal position 266 to its open position 262. The priming and supply valve 288 shifts from its normal position 290 to the position 292. Similarly, the solenoid valve 296 shifts from its normal position 302 to its prime position 308. Therefore, a direct path exists from tubing 254 through tubing 264 and 284, 286 through valve 288 and tubing 294 through valve 296 and through tubing 298 to the suction side of the compressor 300. The compressor 300 is conductively connected via conductor 326 to the control means 280 and receives an operation signal. In particular, the electric motor starts causing the compressor to draw a suction to thereby evacuate all of the tubing as hereinbefore described. Upon achieving a preselected vacuum or negative pressure, or if desired by the user after a preselected period of time, the control means 280 supplies a signal to the solenoids 296 and 288 to cause them to shift to their respective normal positions 302 and 290, and if desired to turn off the compressor 300. Solenoid 260 remains in its open position 262. Therefore, helium is supplied from the accumulator 316 through regulator valve 314 and pressure regulator 312 to backfill a specific metered amount determined by the pressure selected on the bleed valve 314 and pressure regulator 312 and the time which valve 260 (FIG. 6) remains in position 262. Accordingly, a balloon, such as balloon 72 (FIG. 2), and all the interconnecting tubing including channel 64 is back-filled with a preselected amount of helium. After a preselected period of time or upon attaining a preselected pressure as determined by the pressure transducer 322, a signal reflective thereof is supplied to the control means 280 via conductor 324 to in turn cause the solenoid valve 260 to return to its normal closed position as indicated by the solid line 266.

As shown in FIG. 7, the air actuation means 282 is a system having a compressor 300 which supplies pressurized air to an accumulator 325 and via tubing 326 to solenoid valve 327B. The compressor 300 is connected to the control means 280 by conductor 326 to receive start and stop signals therefrom when the pressure in tubing 326 as sensed by pressure transducer 333 supplied by signal via conductor 335 to the control 24 is below a preselected low (start or power supplied) and is at or above a preselected high (stop or power removed). In the event of system malfunction, a pressure relief valve 337 is connected to relieve excess pressure in a normal manner.

The air pressure supplied by the compressor 300 and accumulator 325 arrangement is supplied via tubing 326 through the solenoid valve 327B to tubing 236 and 234 (FIG. 6) to the air actuated piston 216. The solenoid valves 327B is normally open as indicated by the solid lines 339B to connect the tubing 236 to atmosphere through a vent line 335B and a muffler 337B. The valve 327B receives an operate signal to cause balloon inflation from the control means 280 via conductor 340B to cause it to shift to the pressurize position shown by dotted lines 341B. Air pressure is thus ported directly through the tubing 236 and 234 to move the piston 228 (FIG. 6) and in turn cause the plunger 206 to pump the helium in the cavity 210 into the balloon such as balloon 72 of FIG. 2. After a predetermined period of time at which the balloon is inflated at a selected pressure (as sensed by transducer 256), the control means 280 causes the valve 327B to move to its normal position 339B to deflate the balloon.

It should be noted that a second solenoid valve 327A is here used for safety. That is, both valves 327A and 327B have a normal and failed position which is the vent position 339A and 339B. Thus, any system failure (e.g., loss of power, solenoid failure) will result in venting and the operation of the balloon to a deflated condition. Thus, the imposed occlusion effected by the balloon is removed to eliminate the threat of an over-pressure condition in the retroperfused region. An appropriate alarm, (audible, visual or both) may be actuated in the event of such a failure to alert the operator. It should be noted that safety valve 327A operates between its normally open or vent position 339A and its closed position 341A in which it is connected to a sealed vent 335A. It receives control signals from the control means 280 via conductor 340A to move to the closed position 341A at the same time valve 327B moves to the position 341B. However, safety valve 327A also receives control signals to move to the open position 339A whenever an unsafe condition is detected by the control means and balloon deflation is required. Further, the vent 337A and interconnecting tubing 343 are sized large enough to depressurize the air actuated piston 216 so the spring 238 (FIG. 6) will cause piston 228 movement and in turn balloon deflation even though valve 327B is defective and remains in position 341B.

Referring again to FIG. 7, the control means 280 is here depicted to show a series of operating controls and indicators. In particular, a calibrated operation control or knob 328 is provided which is a control to set in this embodiment the maximum occluded sinus pressure. That is, the knob 328 sets a preset signal reflective of a pressure which may be regarded as the maximum sinus pressure to be detected by the pressure detection means and more particularly the pressure transducer 270. The maximum sinus pressure signal set by knob 328 is compared to the pressure signal received from the transducer 270 via conductor 276. If the pressure signal received via conductor 276 equals or exceeds the maximum sinus pressure signal set by knob 328, the balloon inflation means 195 (FIG. 6) is activated to cause the balloon to be put in its deflated condition. The maximum sinus pressure is selected as hereinafter described and in any event at or below the maximum regarded to be safe by the user based on his medical experience such as 60 mm Hg for an adult person.

A minimum sinus pressure control or knob 330 is also provided. A minimum sinus pressure may be desired in order to facilitate retrograde perfusion. That is, a minimum pressure may reflect complete or an acceptable level of drainage in the region so that retroperfusion can be again commenced by occluding the lumen and increasing coronary sinus pressure. A signal reflective of the desired minimum sinus pressure can be set via control or knob 330 via circuitry hereinafter discussed. The minimum sinus pressure is compared with the sinus pressure signal received via conductor 276 from transducer 270 in order to cause the balloon operation means 195 to activate to cause the balloon, such as balloon 72, to be placed in its inflated condition upon obtaining or going below the minimum sinus pressure signal set by knob 330.

The control means 280 also includes a retroperfusate pump speed control 332 and a pump operation control 334. The pump operation control 334 is an on-off switch of any convenient design or type, as desired by the user. Indeed, the pump on-off control 332 can even be combined with the pump speed control 332, if desired. Here, it is preferred to have them separate so that a selected pump speed may remain set even though the system is deactivated for a period of time. The pump speed control 332 is simply a conventional variable speed control which causes the pump 172 and more particularly the pump motor 194 (FIG. 6) to operate faster or slower through associated circuitry, as hereinafter described. The particular control 332 is here depicted to have a digital readout 332A, 332B and 332C of the flow rate selected by manipulation of thumb wheels 332D, 332E and 332F.

The control means 280 also includes a system activation control 336 which is simply an on-off power switch. Here again, it may be of any convenient design or type as selected by the user. In simplified form, the on-off control 336 operates to receive power from an external source which is here shown to be an external source via conductor 338 and 340. The source is a conventional source of 115 volt electrical power. The power may also be received from a continuously charged battery 342 which may be incorporated into the control means 280 or separately provided as desired by the user.

The control means 280 also includes a maximum inflation time control 344 and a minimum deflation time control 346. These controls are associated with timers which are described more fully hereinafter which time the maximum amount of time the balloon, such as balloon 72 (FIG. 2), is in the inflated condition (receiving an inflation operation signal) and the amount of time it is in a deflated condition (receiving a deflation signal). In operation, the maximum inflation time is set so that whether or not the maximum sinus pressure as set with knob 328 is ever attained, the balloon 72 is put in its deflated condition upon attainment of the maximum inflation time. On the other hand, the minimum deflation time is set so that the balloon 72 remains deflated at least for a specific minimum period of time. That is, for inflation to occur both the selected minimum time and minimum pressure must be attained. The controls 344 and 346 are also thumb wheel switches with associated digital readout of the valve set in similarly to control 332.

The control means 280 also includes a visual indicator 348 of actual sinus pressure and a second visual indicator 350 which displays on a calibrated scale the maximum sinus pressure set by knob 328, the minimum sinus pressure as set by knob 330 and the mean sinus pressure actually being determined or calculated by electronic circuitry in the control means 280, as hereinafter described. Also shown is a series of visual alarm indicators 351 discussed in more detail hereinafter.

Control Circuitry

Figure 8:
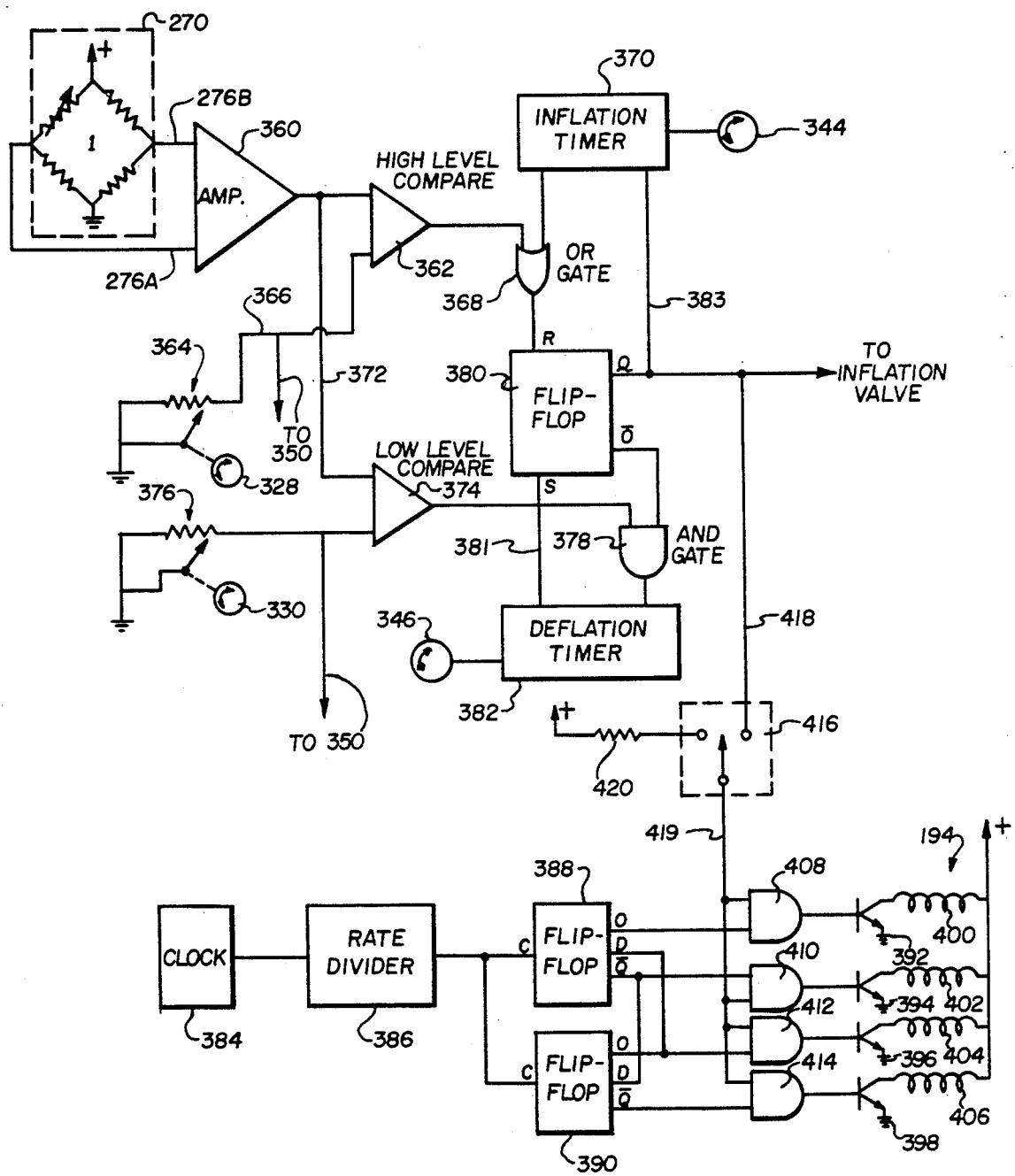
FIG. 8 is a simplified block diagram of the logic circuitry of the control means of the driver for operation of the balloon inflation means of the instant invention.

FIG. 8 is a simplified representative diagram of portions of the circuitry of the control means 280 (FIG. 7) with other representative components selected for clarity. In particular, the pressure transducer 270 of FIG. 6 is here shown in FIG. 8 to be an electrical bridge with a variable leg which is in fact varied based on the pressure detected by the pressure transducer. The output thereof is a pressure reflective signal that is supplied via conductor 276 (which is here shown to be conductors 276A and 276B) to components which are extant in the control means 280. In particular, the output of the pressure transducer 270 is received by an amplifier 360. The amplifier supplies its output to a high level comparator 362 which also receives a comparison signal from the maximum sinus pressure control knob 328 which sets that signal through a variable resistor 364 and supplies that signal via conductor 366 to the high level comparator 362. The output of the high level comparator 362 is supplied to an OR gate 368. The OR gate 368 receives another input from the inflation timer 370 which also receives a preset signal from the control knob 344.

The output of the amplifier 360 is also supplied via conductor 372 to the low level comparator 374. The low level comparator 374 also receives another input from the minimum sinus pressure control knob 330 which sets the appropriate signal via a variable resistor 376. The output of the low level comparator 374 is supplied to an AND gate 378.

Variable input comparators 362 and 374 establish the upper and lower limits of the allowable pressure in, for example, the coronary sinus as detected by the transducer 270, as hereinbefore described. An RS flip-flop 380 controls the inflation valves 327A and 327B as well as the two timers 370 and 372. Prior to balloon inflation in, for example, the coronary sinus, the pressure must have dropped below the lower preset limit which may be set, for example, to a patient's base line coronary sinus pressure as determined by base line determination procedures more fully discussed hereinafter. When the pressure detected by the transducer 270 in the coronary sinus drops below the preset, the low level comparator 374 goes high. This high signal is combined in an AND gate 378 with the appropriate logic from the flip-flop 380. The deflation or delay timer 382, which started when the flip-flop signal indicated deflation counts to the time preset by the control knob 346. When the deflation timer runs out, the flip-flop 380 is reset via conductor 381 and the appropriate inflation valves 327A and 327B (FIG. 7) are activated to operate the air actuated piston 216 (FIG. 6). Simultaneously, the inflation timer 370 is started by a signal sent via conductor 383 and runs out to the time preset by control knob 344 or until the maximum coronary sinus pressure as measured by the pressure transducer 270 is received through the high level comparator 362, the output of which causes flip-flop 380 to reset through the OR gate 368. The upper and lower pressure limits as set via knobs 328 and 330 are supplied through appropriate means, as hereinafter discussed, to the indicator thereof 350 on the control means 280.

As noted hereinbefore, the roller pump 174 (FIG. 6) is driven by a stepper motor. The rate of pumping or speed of the pump is dictated by the pulse rate delivered to the motor from a clock or oscillator 384 (FIG. 8) and a digital rate divider 386. A pair of JK flip-flops 388 and 390 generate the required sequential logic to switch the power transistors 392, 394, 396 and 398 attached to the motor coil 400, 402, 404 and 406. A series of AND gates 408, 410, 412 and 414 are connected through switch 416 which may be operated to a first position in connection with the output of flip-flop 380 to receive signals therefrom via conductor 418 to be operated in synchronization with balloon inflation. The switch 416 may alternately be positioned to be in connection with the power source through resistor 420 and on-off switch 334 (FIG. 7) and pump speed switch 332 for continuous operation at a preselected speed.

Figure 9:
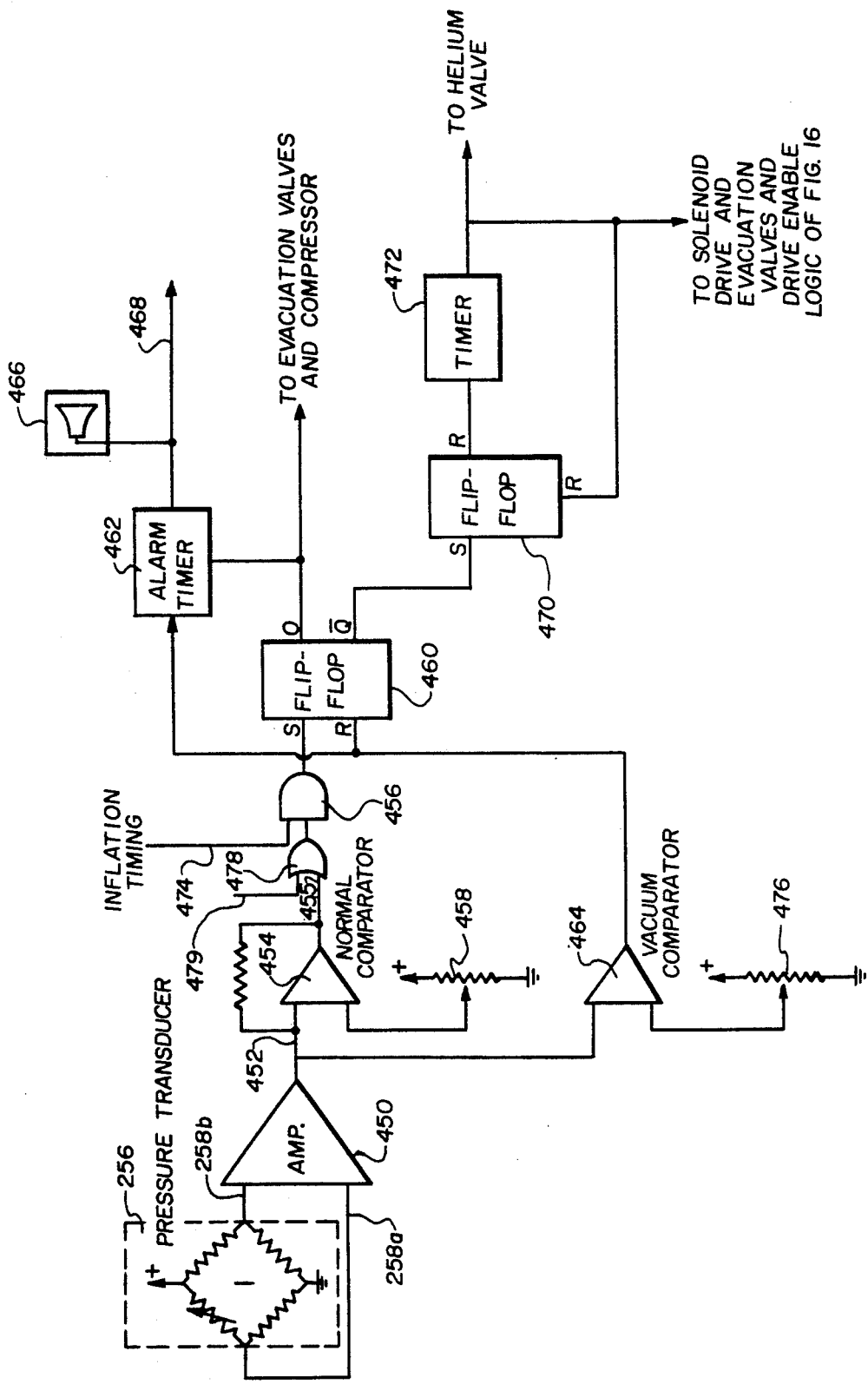
FIG. 9 is a simplified block diagram of a portion of the control means for operation of the priming system associated with the balloon inflation means of the instant invention.

Referring now to FIG. 9, a simplified diagram of priming system controls is depicted with the pressure transducer 256 (FIG. 6) shown electrically in FIG. 9 as a bridge. It supplies a pressure reflective signal via conductors 258A and 258B to an amplifier 450. The output of the amplifier 450 is supplied via interconnecting conductors 452 to a comparator 454, the output of which is further supplied to an AND gate 456 via conductor 455.

Figure 12:
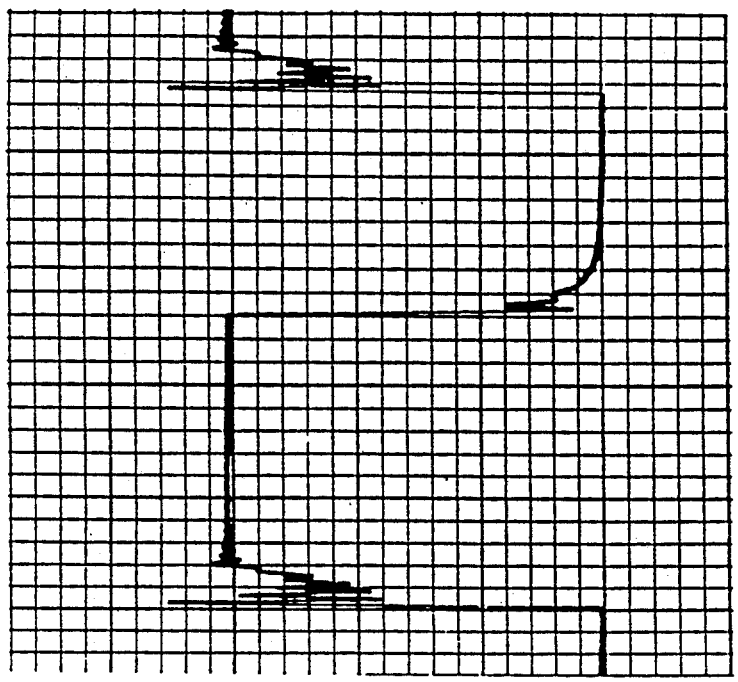
FIGS. 10, 11 and 12 are graphs of pressure versus time as a function of the volume of priming fluid inserted by the priming system of the instant invention.
Figure 11:
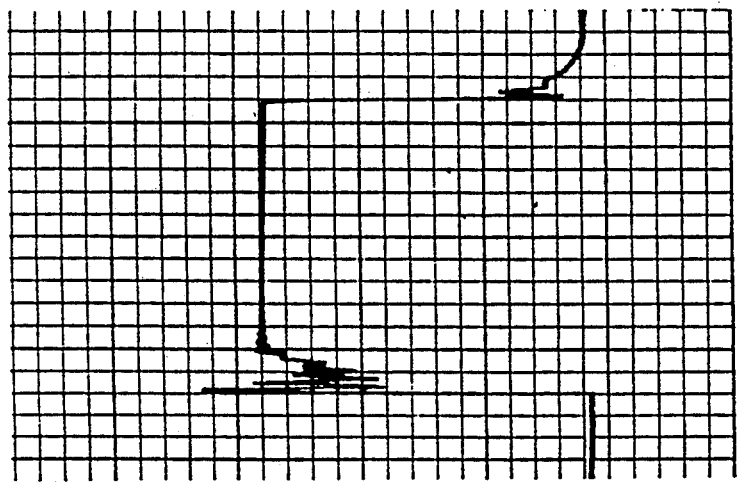
Figure 10:
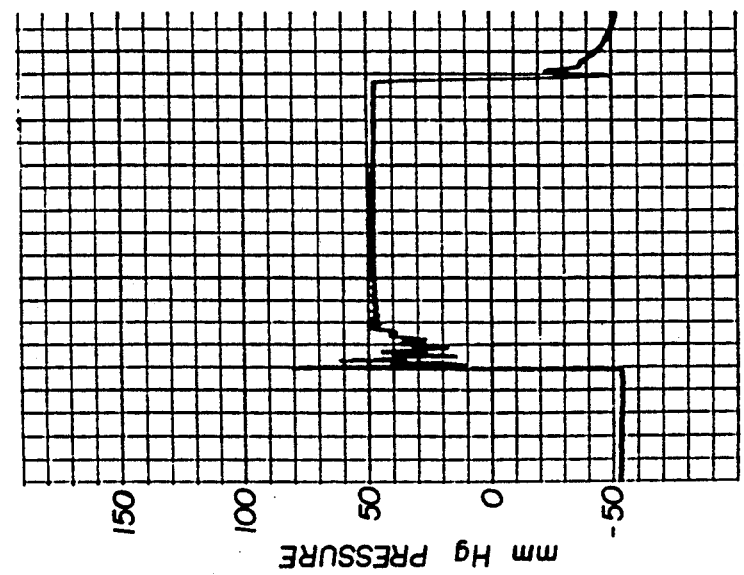

The circuit of FIG. 9, as noted before, controls the priming system and the volume of fluid (gas) in the system monitored by the transducer 256. Under normal circumstances, a graph of pressure as detected by transducer 256 versus time results in a wave form approximating a square wave as depicted in FIGS. 10 through 12. The balloon operation signal is a pressure signal generated as the pump syringe 206 is moved back and forth within the pump body 204 (FIG. 6). FIG. 10 is a wave form which represents the pressure in the balloon when it is inflated and when the system has been primed with about 2.5 cubic centimeters of helium. FIG. 11 is a wave form detected when the system has been primed with about 3.0 cubic centimeters of helium. FIG. 12 reflects priming with about 3.5 cubic centimeters of helium. Comparing FIGS. 10-12, it can be seen that as the volume of priming fluid is increased or decreased, the height or upper level (inflated pressure) of the wave form changes accordingly. The circuitry, as shown in FIG. 9, monitors this pressure using the pressure transducer 256.

The pressure transducer 256 (FIG. 6) produces a continuous output signal reflective of pressure in line 200 which signal is amplified by the amplifier 450 and compared to a preset signal reflective of a desired operating normal pressure range which is preset in via variable resistor 458. When the pressure as detected by transducer 256 gets out of the normal hysteresis range (above or below) of the comparator, or on system initialization (turn on), operation of the actuator 198 (FIG. 6) is discontinued or interrupted and the system put in a condition wherein the balloon is deflated. Thereafter a priming sequence is begun. A change in the output signal from the comparator 454 means that either the balloon (e.g., balloon 72, FIG. 2) has lost or gained pressure (i.e., fluid) due to diffusion of gas from or into the balloon. It should be noted that in operation the pressure as actually risen from what is believed to be the diffusion of blood gases through the balloon 72 into the interior of the balloon 72. The change in output signal on conductor 455 passes through the AND gate 456 to set a latch, which is here shown to be flip-flop 460. The latch, in turn, starts a timer 462. The latch 460 also sends control signals to operate the compressor 300 and to operate the priming or evacuation valves 308, 288 and 260 in order to generate a negative pressure to obtain a vacuum in the system including tubing 200, 212, 213, 256, channel 64, chamber 210 and balloon 72. Optionally, a signal may also be set to interrupt or stop the pump 172 (FIG. 6). If the timer 462 reaches a preset time before an appropriate negative pressure (vacuum) is detected by pressure transducer 256 and in turn by a second or a vacuum comparator 464 (FIG. 9), the balloon 72 (FIG. 2) is assumed to have failed. Operation of the system in its entirety is shut down and an alarm, which is here preferably selected to be an audible alarm 466, is sounded. Optionally a visual alarm 467 (FIG. 7) may be illuminated. Shut down is effected by a disable signal to the circuitry to stop all operation through disable control logic via conductor 468.

If a negative pressure is detected by the transducer 256 and in turn by the comparator 464 within the appropriate time as set by timer 462, the output of pressure transducer 256 via amplifier 450 and vacuum comparator 464 causes the flip-flop or latch 460 to activate. In turn, a second latch 470 operates to introduce fluid. More particularly, helium from the source 316 (FIG. 7) is supplied through the associated solenoid valves 288 (FIG. 7) and 260 (FIG. 6) upon receipt of control signals from the latch 470 through the timer 472. The amount of helium introduced is controlled or metered by timer 472 so that the helium is introduced to the system for a fixed period of time at a known flow which is controlled by the flow regulator 312 (FIG. 7). When the appropriate time has elapsed, the timer 472 resets all of the latches 470 and 460 and in turn returns valve 260 to its normal position 266 (FIG. 6). Further, it also supplies control signals to the balloon operation means 195 and more particularly valves 327A and 327B to return it to operation. In turn, the pump 202 returns to normal operation to cause the balloon to be sequentially operated between its deflated and inflated conditions, as hereinbefore described. Also optionally, the pump 172 may be enabled for normal operation. Priming system operation can also manually be effected at any time by operation of the priming switch 477 on the control means (FIG. 7). An OR gate 478 is interconnected on line 455 to pass the output of the normal operator 454 to initiate priming or to receive the manual prime signal from switch 477 via conductor 479.

Referring again to FIG. 9, it should be noted that the inflation time signal is received from the inflation timer 370 (FIG. 8) via conductor 474 by the AND circuit 456. The inflation timing signal is used to allow the output of the normal comparator 454 to be passed or to sample the pressure signal output from the amplifier 450 only during the period of balloon inflation.

It should be noted that the level of vacuum acceptable is preset by a variable resistor which is supplied to the vacuum comparator 464. This value is set manually by adjustment of variable resistor 476.

Figure 13:
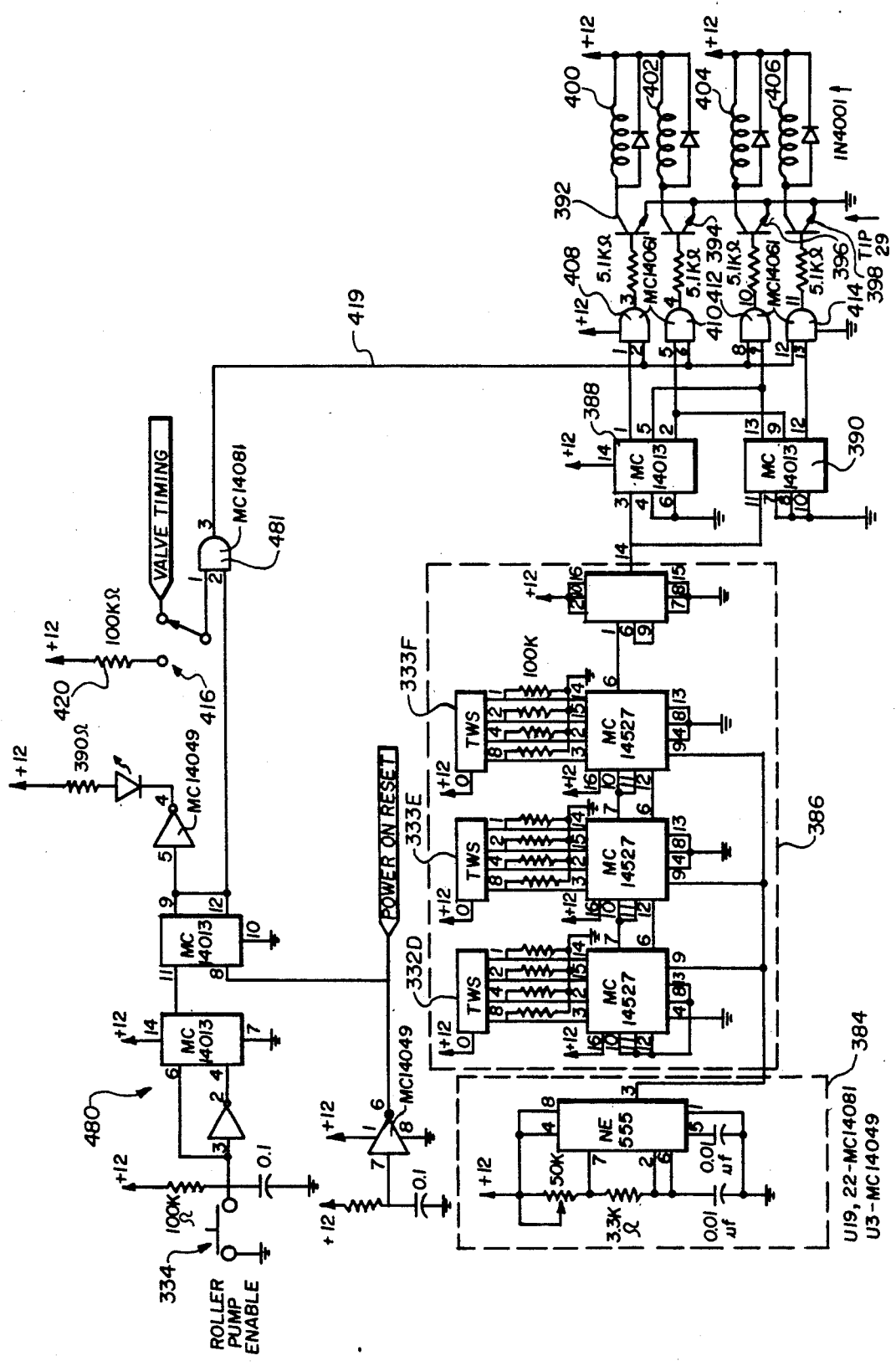
FIG. 13 is a detailed circuit diagram of that portion of the control means for controlling the pump means, and more particularly the electric motor that drives the pump means of the instant invention.

Referring now to FIG. 13, the detailed circuit diagram of the components that control the roller pump 172 are depicted. The roller pump enable switch 334 (FIG. 6) is shown as a single push-pull or push button switch in FIG. 13. Since it is preferred to have a waterproof push-button type switch due to expected use in a hospital environment, a sealed type switch with latching circuitry 480 is shown. Also shown is a clock 384 (FIG. 8) and a rate divider circuit 386 (FIG. 8) which receives a manual signal from thumb wheel switches 332D, 332E and 332F (FIG. 7). The divider 386 supplies its output through flip-flops 388 and 390 and a series of AND circuits 408, 410, 412 and 414 directly to the stepper motor windings 400, 402, 404 and 406 via power transistors 392, 394, 396 and 398. The AND circuits 408, 410, 412 and 414 are connected to receive an input from the valve timing circuitry via conductor 419 as hereinbefore noted. That is, it may be desirable to stop operation of the pump 172 (FIG. 6) when the balloon 72 is in a deflated condition. In some applications, drainage may be not as effective if retroperfusate is continuously injected during periods of deflation. Thus, the system herein disclosed may be arranged by providing a switch 416 so that pump 172 operation is effected only when the system has placed the balloon 72 in an inflated condition. The AND gate 481 allows for the operated signal from valve timing to pass only when the pump switch 334 is operated to an "on" condition.

Figure 14:
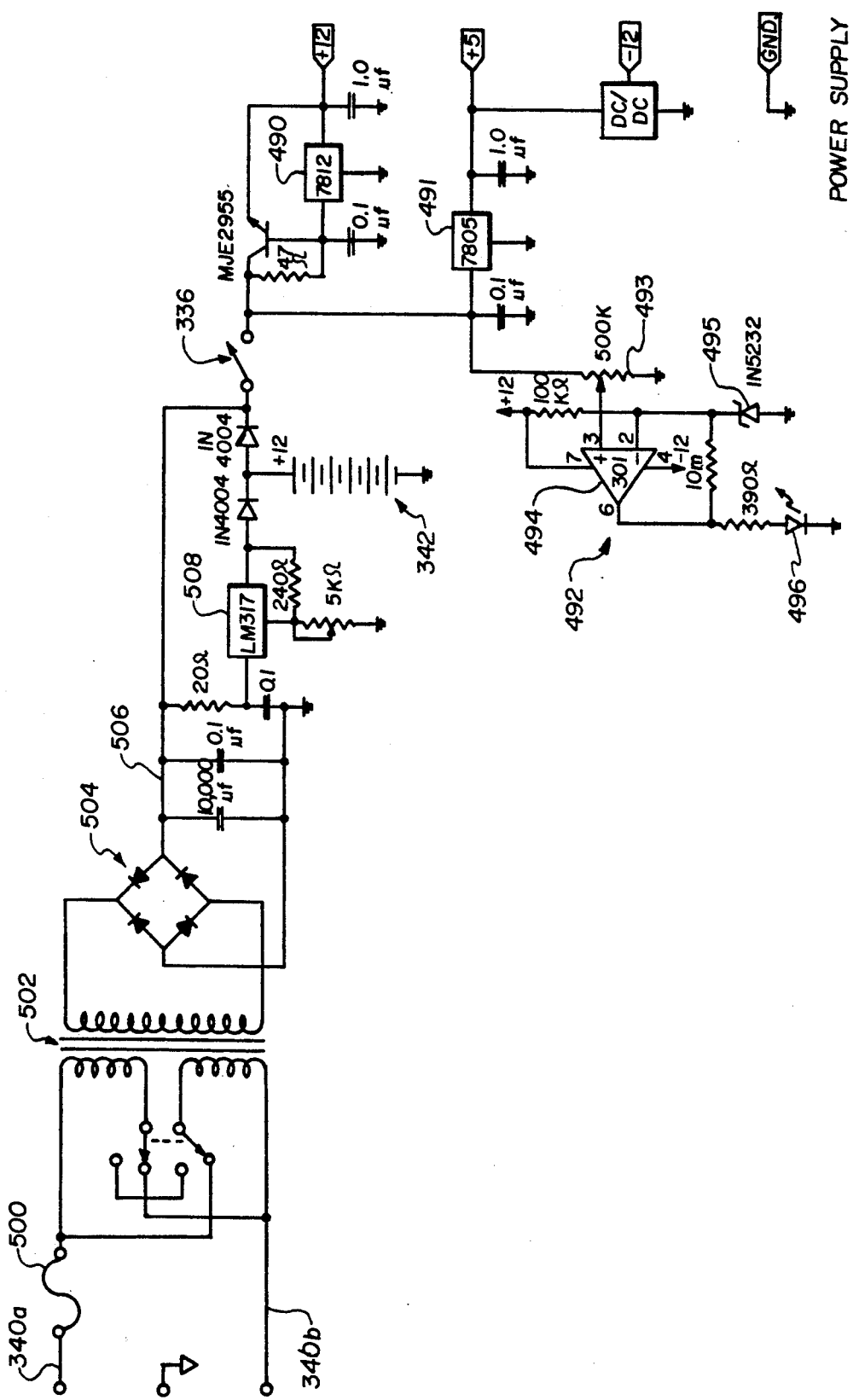
FIG. 14 is a detailed circuit diagram of the internal power supply of a control means of the instant invention.

The power supply for the system is depicted in FIG. 14. The power from an outside electrical source such as a 115 volt outlet power is received via conductors 340A, 340B through a fuse 500 and through an isolation transformer 502 and a full wave rectifier 504. The output of the full wave rectifier is filtered by a series of filters 506. The output is then supplied through the system on-off switch 336 (FIG. 7) to various circuits to supply and develop the necessary requisite voltages for use by the various components throughout the system. The various power supply lines throughout the system have not been shown for simplification. Those skilled in the art will recognize that power from the various components is to be delivered in accordance with the needs of the various circuits and the various components thereof.

It should also be noted that FIG. 14 shows a battery 342. The battery is continuously charged by the output of the full wave rectifier 504. The voltage from the full wave rectifier is selected to be slightly higher than the fully charged battery 342 which is being continuously charged. If power from the rectifier 504 falls below the battery 342 voltage, the system automatically draws from the now higher power source, the battery 342. A current limiter 508 acts to prevent over-charging of the battery. Also, voltage regulators 490 and 491 provide for additional regulation and supply of desired supply voltages. Further, detection circuitry 492 is provided to detect a low battery voltage condition. That is, low voltage through switch 336 can occur only if the output of the rectifier 504 and battery 342 are both below a selected minimum. In that case, the battery 342 will be the operative source of power. A divider 493 is set to supply live voltage to a comparator 494 for comparison to a reference voltage received from a diode 495. If the comparison falls below a selected minimum, LED 496 is illuminated to visually activate the alarm 497 on FIG. 7.

Figure 15:
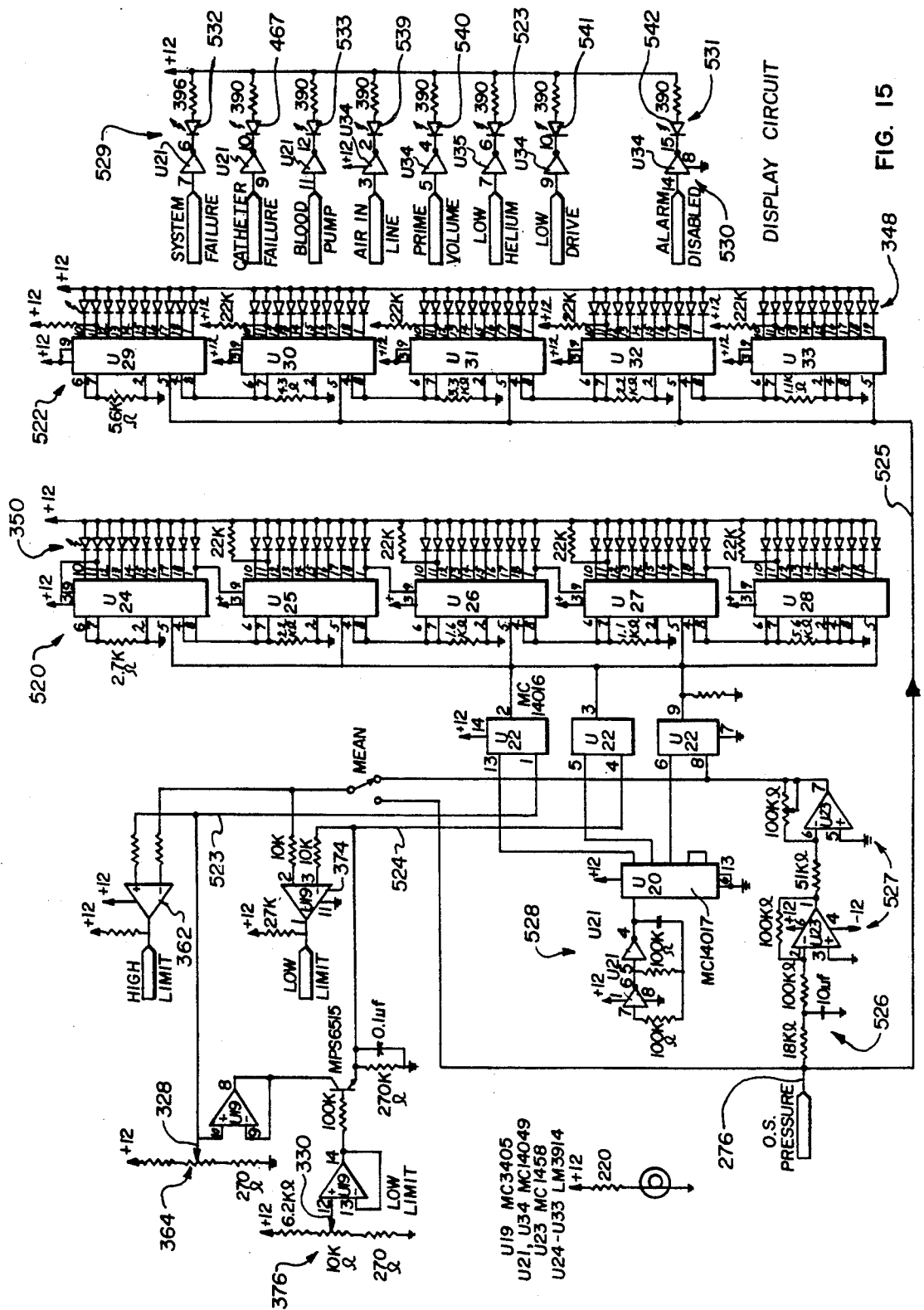
FIG. 15 is a detailed circuit diagram of certain display circuitry of the control means of the instant invention.

Referring now to FIG. 15, various circuits for the display 351 are illustrated. Principally two elongated stacks of LED's 348 and 350 (FIG. 7) are shown. The LED's are illuminated or activated by appropriate control circuitry and comparators 520 and 522. It should be understood that the visual indication perceived visually on the indicators 348 and 350 is a series of lights that appear on a vertical scale calibrated to reflect pressure values. Each LED moving from the bottom to the top is visually perceived on FIG. 7 to relate to a preselected unit of pressure which has been here selected to be two millimeters (mm) of mercury (Hg) for each LED.

The principal indications on the display 350 include the preset maximum sinus pressure or high limit set by knob 328 and the minimum sinus pressure set by knob 330. These signals are supplied via conductors 523 and 524. The actual coronary sinus pressure signal is received from transducer 270 (FIG. 6) via conductor 276 and supplied via conductor 525 for direct display by indicators 348. The actual coronary sinus pressure is also supplied through a filter 526 to circuit 527 to calculate the mean sinus pressure continuously. The mean sinus pressure is the actual mathematical mean of the coronary sinus pressure signal received via conductor 276. An oscillator circuit 528 is connected to pulse the display LED's 350 at a high rate not visually perceptible so that data changes and indication changes can be discretely calculated and made for a perceived continuous display.

The circuitry also includes a series of optional alarms which may be audible or visual or both. The visual alarms are activated as depicted by circuitry 529. That is, an alarm signal is received from an appropriate detection point in the control means 280 (FIG. 7) and supplied to a respective driver 530 to illuminate its associated LED 531. Thus, a visual indication of the alarm condition appears on the indicator 351 of the control means 280. For example, system failure 532 may be illuminated by prolonged high pressure or excessive pressure in the coronary sinus as determined by a timer either during inflation or particularly during deflation. Also, inflation signals to the inflation valves 327A and 327B can be monitored to detect excessive periods of inflation.

Failure of the balloon would be evident if coronary (lumen) pressure did not increase when control signals are being generated to cause balloon inflation and confirmed by the inability to draw a vacuum (preset negative pressure during prime. Also, insufficient helium supply would effect the ability to occlude. A timing or logic circuit to detect these conditions may supply a signal to illuminate the catheter failure alarm 467.

Failure of the retroperfusate pump and more particularly the motor 194 can be detected by monitoring for excessive current to the motor windings such as winding 400 (FIG. 13). Excessive current would indicate that the winding has failed or the motor has stalled. A current detector in the conductor to the motor may be constructed to supply an alarm signal to activate a blood pump alarm light 533.

Figure 19:
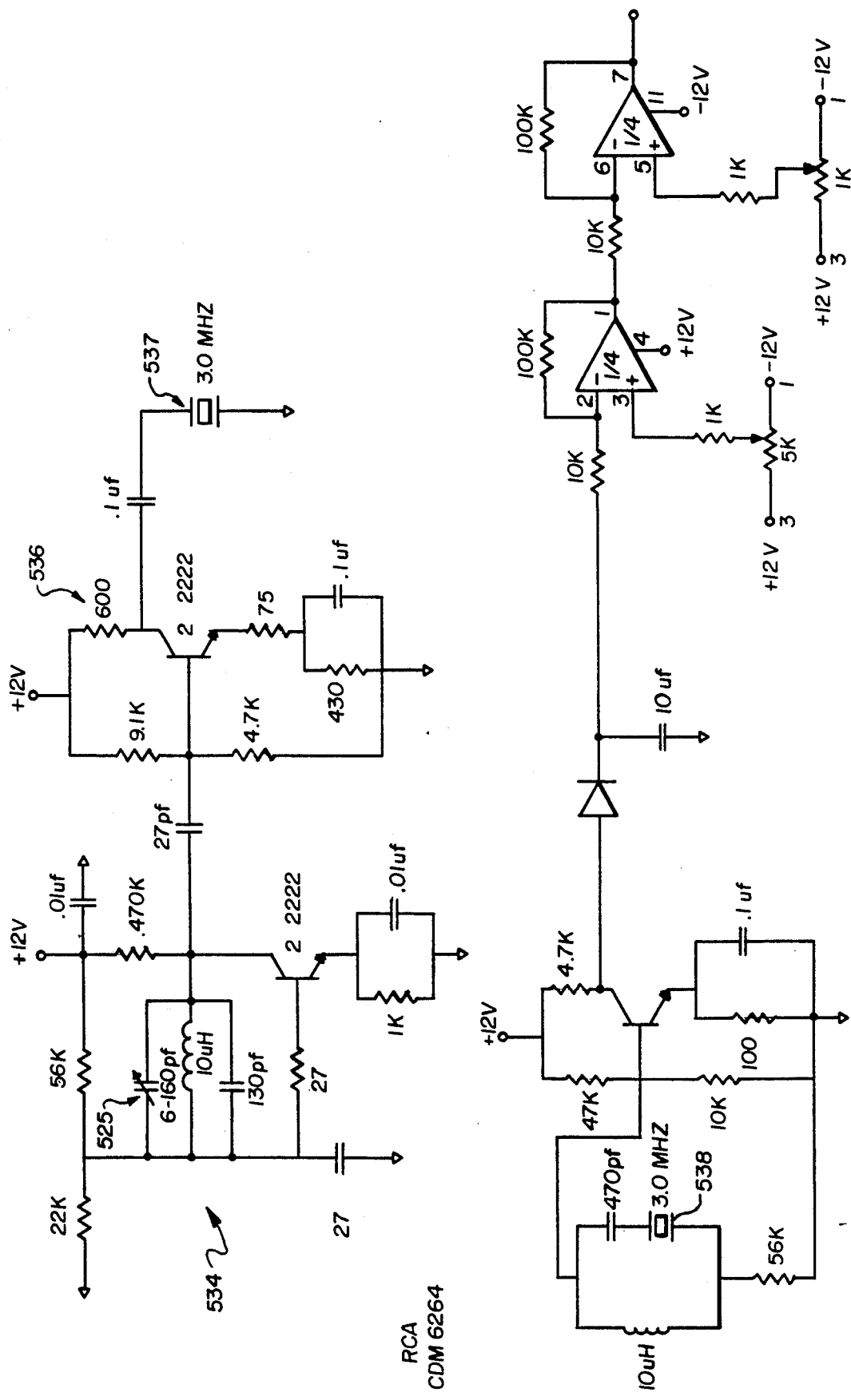
FIG. 19 is a circuit diagram of detection circuitry to detect air in the retroperfusate.

Since the retroperfusate is being processed through an external system, there is the risk of introducing air into the retroperfusate and in turn causing an air embolism by injecting that air into the lumen. An air detector may be placed either at the inlet 186 or outlet 188 of the pump 172 to detect air. FIG. 19 is a circuit diagram for an ultrasonic detector for detecting air entrained in the retroperfusate.

FIG. 19 depicts an oscillator circuit 534 which may be tuned by a tuning capacitor 525. The output of the oscillator 534 is supplied to a driver 536 to activate an acoustic oscillator or transducer 537. The output of the oscillator 537 is passed through the retroperfusate and received by another transducer 538 which is appropriately pretuned. The output thereof is processed to detect signal level since the sound received will be reduced with air entrained in the retroperfusate due to scattering. The output is supplied via amplifiers to illuminate the alarm indicator 539 (FIG. 7).

Improper prime volume in the syringe or chamber 210 to effect proper occlusion may be ascertained by the steady state occluded pressure level as detected by transducer 256 (FIG. 6). With an appropriate integrator, timer or delay circuit, an alarm signal can be generated to illuminate alarm indicator 540 (FIG. 7) and to cause a priming sequence to be initiated as hereinbefore discussed.

A low drive pressure alarm signal can be generated by pressure transducer 333 which also causes the compressor 300 (FIG. 7) to operate. If an associated timer in the control means 280 counts down a present time before the pressure returns by action of the compressor 300 to a normal preselected range, then a signal may be sent to activate the low drive pressure alarm 541.

The alarm disable switch may be provided to disable all alarm functions. This may be desirable for experimental use or use in unusual clinical cases where certain pressures may not be reached. Activation of such a switch may be used to indicate by illumination of a disable light 542 on the control means 280 (FIG. 7).

Figure 16:
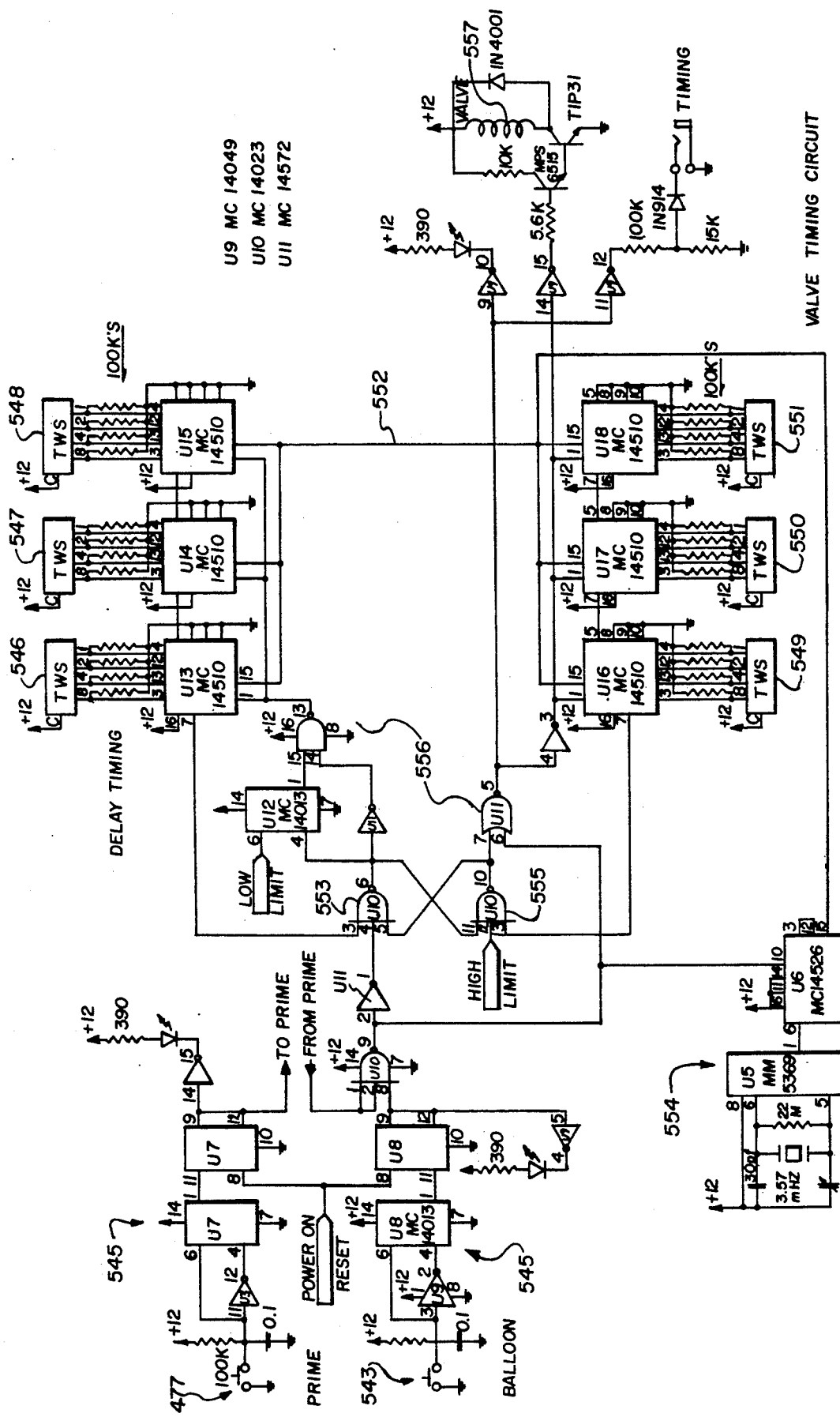
FIG. 16 is a detailed circuit diagram of portions of the control means of the driver of the instant invention for controlling the operation of the solenoid valve of the driver.

Referring now to FIG. 16, the various circuitry for valve timing is shown in detail. The individual switch 477 for initiating a priming sequence is shown. Also shown is the balloon switch 543 which is operated to manually cause the balloon operating means to inflate the balloon (on condition) or deflate the balloon (off condition). Both switches 477 and 543 are push button types with associated latch circuits 544 and 545 respectively.

FIG. 16 also shows the inflation timing signal preset by thumb wheel switches 546, 547 and 548, and delay timing thumb wheel switches 459, 550 and 551. The output of switches 477 and 543 to enable an oscillator circuit 554 which provides clock pulses to the timers via 552. NAND gates 555 and 553 form an R.S. (Reset-Set) flip-flop controlled by the outputs of the timers and the limit comparators through gate 556 to control, for example, the solenoid 557 of solenoid valve 327B (FIG. 7).

Figure 17:
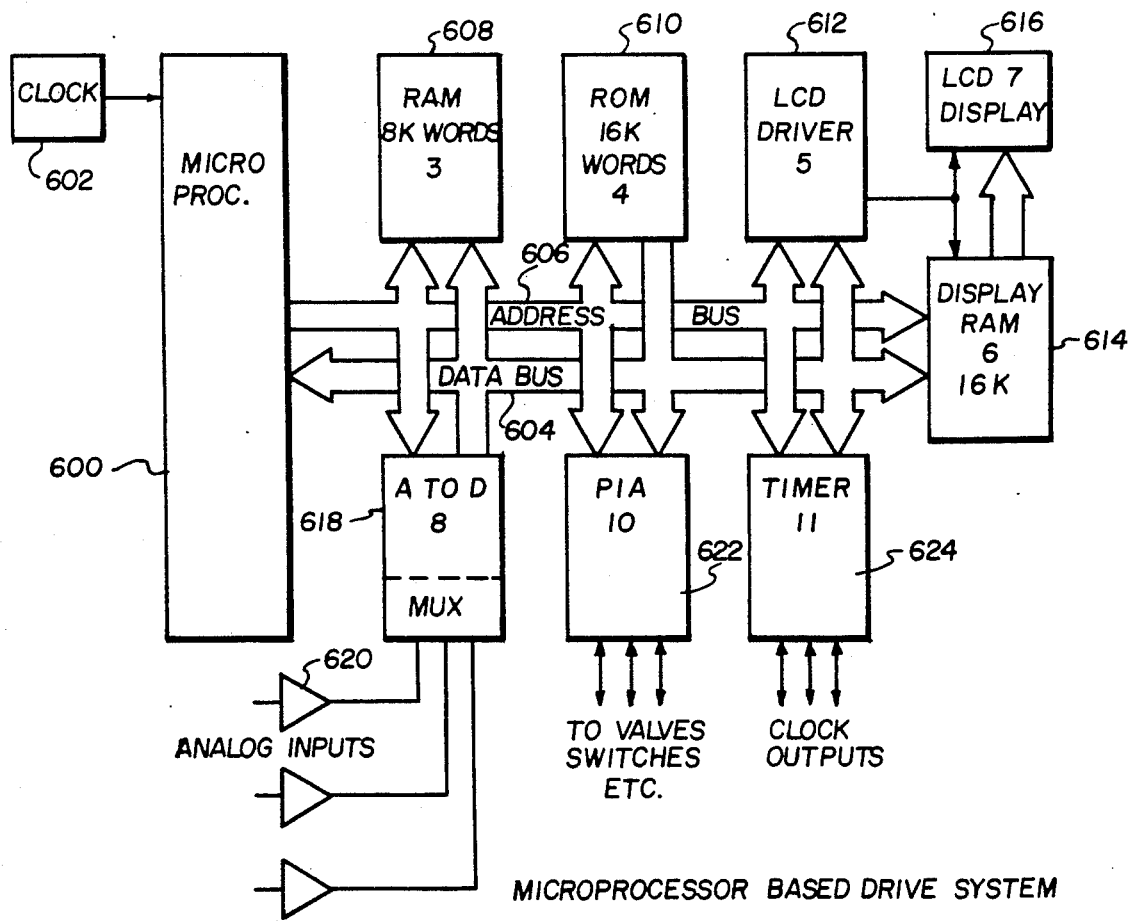
FIG. 17 is a block diagram of a microprocessor based control means for the system of the instant invention.

All of the tasks accomplished by the circuitry as illustrated in FIGS. 13, 14, 15 and 16 may also be accomplished by using a microprocessor based system. The logic incorporated in the discrete circuits therein illustrated may readily be programmed into a microprocessor system. The microprocessor is able to evaluate the coronary sinus pressure signals and other analog parameters and automatically operate the components of a retroperfusion system in a manner as hereinbefore described. The control means, which is microprocessor based, is depicted in FIG. 17. It includes a microprocessor 600 (e.g., Motorolla 68000) and a clock circuit 602 assembled in a manner known to those skilled in the art. The microprocessor 600 in turn controls a number of peripherials through its data and address buses 604 and 606. The temporary data is stored in a random access memory 608. The program is stored in a read only memory 610. A display controller 612 drives a block of random access memory 614 and a liquid crystal display matrix 616. The random access memory 614 holds only the information to be displayed by the display 616.

An analog to digital converter and an input multiplexer 618 receives up to eight analog input signals (e.g., from transducer 256, FIG. 6) to be read by the microprocessor 600. Each of these inputs is amplified by an isolation amplifier, such as for example, amplifier 620. The amplifiers also act to isolate the patient from hazardous voltages.

A peripherial interface adapter 622 is used to communicate with push buttons or switches on the drive console or chassis, such as the one shown in FIG. 7, or with valves or compressors internal to the entire retrovenous perfusion system. Also, a programmable timer 624 is used to generate time delay signals within the system to drive external systems, such as stepper motors for the roller pump of a driver such as the driver system depicted in FIGS. 6 and 7. A Motorolla 6840 timer includes three separate programmable outputs which are considered here to be particularly suited for the application herein disclosed.

Operation

As noted hereinbefore, the retrograde catheter, such as the catheter 36 illustrated and described with respect to FIG. 2, is principally intended for retrograde perfusion in the coronary sinus region. However, it should be understood that retrograde perfusion may be desired in other organs of the body or in other regions of the body. A catheter employing the principals as herein disclosed and described is particularly suited for retrograde perfusion when appropriately sized and modified for such other region.

Referring specifically to retrograde coronary sinus perfusion, a catheter such as the catheter 36 illustrated in FIG. 2 must first be inserted into the patient and threaded through the venous system into the coronary sinus region. It is presently contemplated that penetration would be made in the subclavian region down through the vena cava and into the coronary sinus region by the use of fluoroscopy procedures. The catheter desirably has a preformed bend 147 such as that illustrated in FIG. 5 so that the catheter 36 may be rotated or manipulated by the user in a conventional manner to thread it through the various portions of the venous system and into the coronary sinus region for precise positioning as desired by the user.

After positioning in the patient, the catheter 36 is desirably connected to a driver 14 such as the driver depicted in FIGS. 6 and 7. The driver, of course, should be first calibrated. That is, pressure transducer 270 should be calibrated by connecting a manometer system such as the manometer associated with standard blood pressure measuring apparatus typically found in a hospital environment. An appropriate maximum pressure may be set through port 272 and established or set in electrically by depression of the maximum push button 329 on the face of the console or chassis 570 of the control means 280 of the driver. Thereafter, the manometer system can be removed and the plug and cap left open to experience atmospheric pressure. Atmospheric pressure can be set in as the zero by depression of the push button 331 on the face of the chassis 380. The calibration port 272 would of course then be appropriately capped or sealed. Of course, before operation, an appropriate supply of pressurized helium would be also provided in the accumulator 316 (FIG. 6). Further, a source of electrical energy would be made available by connection to an appropriate outlet with the plug or cord 340.

Figure 20:
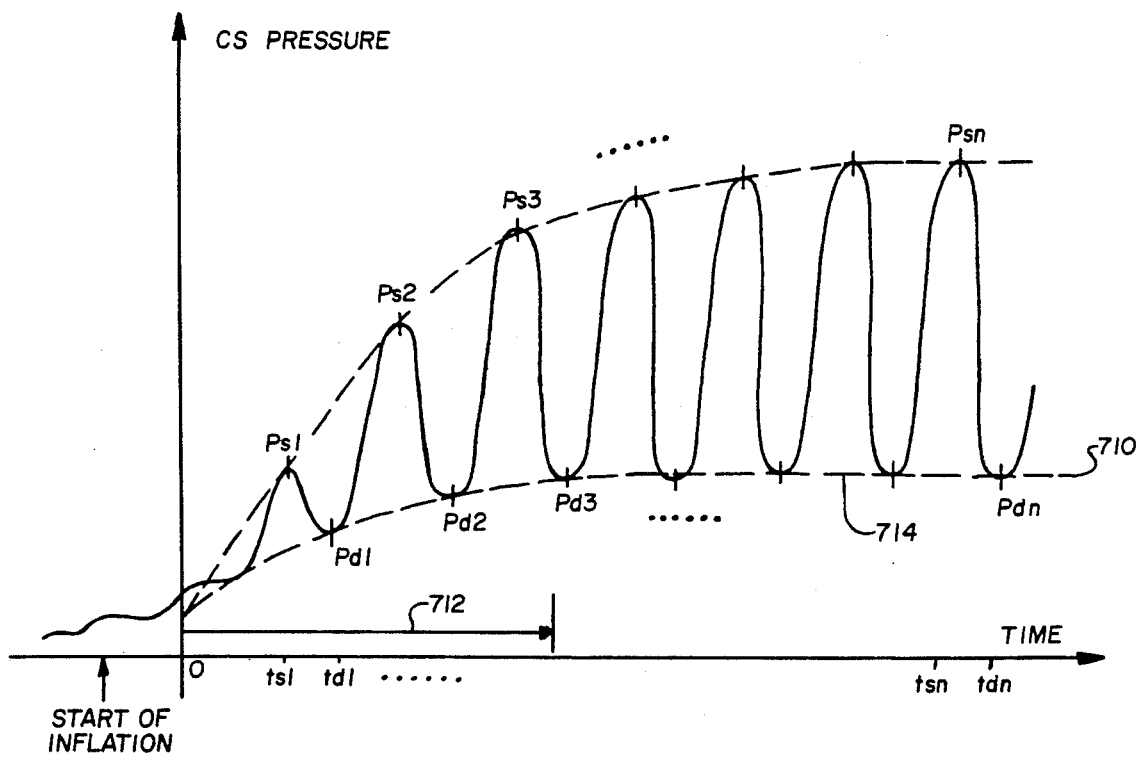
FIG. 20 is a representative, but not actual, graph of coronary sinus pressure with a lumen occluded.

Upon connection of the driver of FIGS. 6 and 7 to catheter 36, system operation can commence. However, preferably it is desirable to obtain a series of base line measurements in order to determine certain pressure characteristics in the coronary sinus region if that information is not otherwise available to the user/operator. In particular, the balloon 72 of the catheter 36 can be manipulated to its inflated condition and deflated condition by manipulation of the appropriate control 543 of the driver. Pressure can be read or detected on indicator 350, and graphed in relation to time. Since the pressure varies between a high at the conclusion of systole (Ps) and a low at the conclusion of diastole (Pd) a constructed graph through the diastole (Pd) points produces a curve 710 as may be seen in FIG. 20 which has a certain rise time 712 before reaching a plateau 714.

Figure 18:
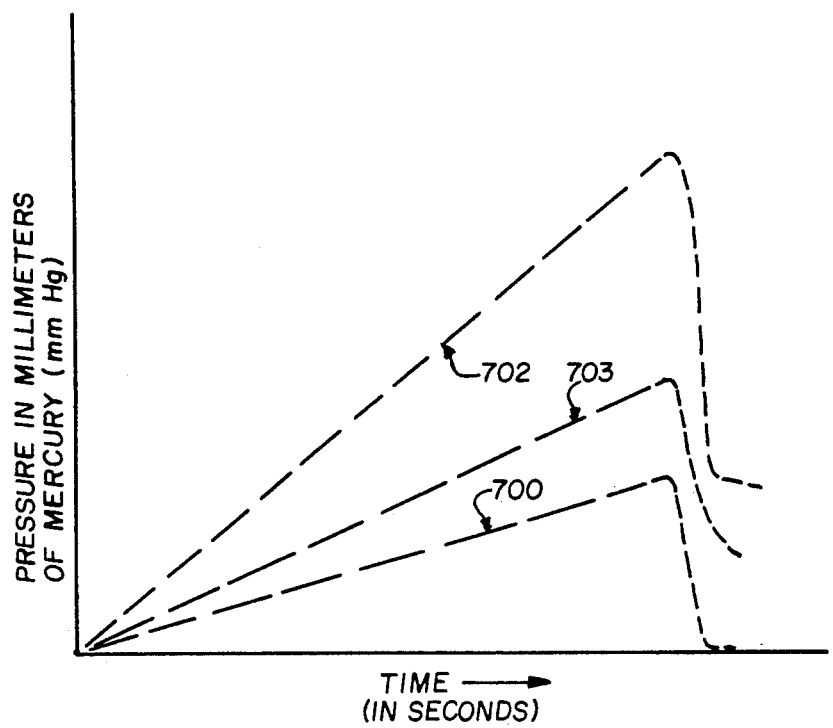
FIG. 18 depicts representative, but not actual, graphs of pressure versus time in the coronary sinus region with the involve lumen occluded and with or without retroperfusate injection.

The objective of this procedure is to determine the expected level or degree of retrograde perfusion that will occur upon the selection of certain operating parameters such as coronary sinus maximum and minimum pressures, operating times, and flow rate of retroperfusate. In other words, it is important to determine what may be viewed in a simple fashion as the efficiency of the retroperfusion therapy. Stated alternatively, the oxygenated blood to be delivered for coronary sinus retroperfusion must migrate through the venous system, through the capillaries and into the myocardial cells. If for some reason the pressure in the arterial system or in the capillaries is relatively high, then the degree of retrograde perfusion and the amount of therapeutic benefit to be obtained will be directly related to the amount of oxygenated blood that can be, so to speak, pushed upstream. In order to obtain an indication of the degree of blockage or resistance to be experienced (recognizing there are numerous other variables involved), the balloon 72 may be put in its inflated condition to occlude the lumen in which it is placed. The pressure as detected by transducer 270 (FIG. 7) is then measured without the injection of retroperfusate. If as shown in FIG. 18, the pressure as monitored rises somewhat as depicted by the graph 700 in FIG. 18, it may be concluded that the amount of blood flowing into the coronary sinus through normal arterial channels is relatively low. Thereafter retroperfusate is injected at a known rate by operation of the supply pump 172 by actuation of switch 334 (FIGS. 6 and 7). The pressure (preferably diastolic) versus time is also then graphed as shown in FIG. 18 by graph 702. A comparison of the two graphs is generally proportional to the volume of retroperfusate being successfully urged upstream and is further indicative of the flow of arterial blood through the normal antegrade channels and of the degree or size of the infarction region. For example, if the difference between graphs 700 and 702 is quite large, it may be deduced that the degree of occlusion on the arterial side is significant and the region affected notable. Accordingly, it may therefore be further deduced by the operator that a significant amount of resistance to the transmission of retroperfusate upstream through the venous system and the capillaries toward the arterial system will be experienced. Similarly, if the pressure as monitored rises quite slowly, such as depicted by the graph 703 in FIG. 18, it can be deduced that the amount of arterial blood flow into the coronary sinus region is proportionally larger so that the amount of flow through the venous and capillary system and into the arterial system is freer or more open. Periodic repetition of the procedure or test may reveal changes in the patient's condition and indicate the then current state or degree of the occlusion and the then current status of normal antegrade flow. This may allow operators to adjust the therapy accordingly.

With such information, the operator using experience should be able to set appropriate times by controls 344 and 346 (FIG. 7) as well as the maximum and minimum pressures by controls 328 and 330 (FIG. 7) for retrovenous perfusion in order to maximize the therapeutic benefit. For example, with a high restriction to flow such as what may be depicted by graph 700 in comparison to graph 702 in FIG. 18, it may be desirable to set the maximum inflation time quite high and to set the maximum sinus pressure as high as may be medically considered permissible in order to maximize the time for retrograde perfusion and indeed migration of the retroperfusate through the venous system and the capillaries and into the arterial system. Similarly, with a high arterial flow indicated by a comparison of graph 700 with 703, one must be cautious to set the maximum inflation time to be relatively low and to set the maximum coronary sinus pressure limit conservatively to avoid any excessive pressures and the concomitant risk of damage to the interior sinus region from excessive pressures stemming from the increased flow and resulted increased pressure buildup from retroperfusion coupled with normal venous flow into the retroperfused region.

After having obtained the initial parameters and an indication of the degree of arterial blockage or infarction, the system may be initialized and operated to perform retrograde perfusion.

As noted earlier, the driver 14 is preferably separated into two structural components. The first supply structure 18 is positioned proximate the patient in order to facilitate use of shorter tubing and in turn incur the benefits of less hemolysis and other related problems associated with extended or lengthy tubing. The control structure 24 is of course positioned generally in the vicinity but remote from the supply structure 18 for operation by the user.

To initialize the apparatus, after connection to the catheter such as the catheter 36 of FIG. 2, the controls of FIG. 7 are set. The maximum and minimum sinus pressure are set by manipulation of knobs 328 and 330, respectively. The desired pump speed is set by manipulation of control 332. The maximum inflation and minimum deflation time are set by manipulation of controls 344 and 346. These controls are all set in order to insure the maximum degree of retrograde perfusion of retroperfusate, such as oxygenated blood, in an upstream fashion in order to minimize ischemia and, of course, avoid necrosis. After initialization by turning the power switch 336 to the on position, the system automatically goes through a priming cycle. That is, control signals are automatically generated to operate valves 260, 288 and 308 to cause the vacuum to be taken from the balloon and for the balloon to be backfilled with helium. It should be noted that helium was selected for physiological reasons as noted hereinbefore. Helium is also desirable because the molecular structure of helium facilitates rapid transmission of the gas through the interconnecting tubing, thus providing for a more rapid priming sequence. After the evacuation and backfill of helium, pump operations can begin by operation of the pump control switch 334 to the on position. In operation, the pump structure 172 continues to supply retroperfusate, which as hereinbefore noted, is oxygenated blood obtained through an appropriate catheter inserted into the femoral artery. Of course, the retroperfusate could also be oxygenated blood from some other source and could also include various therapeutic drugs added to or separately supplied in the supply system of retroperfusate.

During pump 172 operation, pressure detector 270 continuously monitors the pressure in the vicinity of the tip 44 of the catheter of FIG. 2. If the maximum desired sinus pressure is reached, the pump actuation means 198 is operated in order to cause the pump 196 to place the balloon in its deflated condition. In this way, the retroperfusate, such as blood, in the coronary sinus region can drain past the catheter 36. The catheter 36, of course, has been selected and formed as hereinbefore described to have a pressure drop across the balloon 72 of about less than 6 mm Hg so that the blood can drain past the catheter 36 and balloon 72 as rapidly as possible. It should be noted that the pump 172 may continue to operate or may be interrupted at this particular point to avoid further injection of retroperfusate during the deflation period or the draining period. When a minimum sinus pressure is reached and after a minimum amount of deflation time, the balloon 72 is again inflated by a pressure signal sent through the actuation structure 198 and the pump structure 196 to inflate the balloon 72. Of course, at the same time, the pump structure 172 is again operated to cause retroperfusate to be injected into the coronary sinus region. This cycle can be continued without interruption so long as the therapy is desired.

Periodically, when the pressure detected in the balloon inflation system by pressure detector 256 falls outside of a preset range, then the retroperfusion therapy is interrupted and the priming cycle reinitiated so that the balloon system is evacuated and refilled with helium. This will take into account possible loss of helium through migration through the balloon structure, leak joints and otherwise on the gain of gases from the blood by migration through the balloon. Priming may also be manually effected whenever desired. Of course, in the event of a catastrophic failure where a vacuum cannot be obtained in the priming cycle, an alarm is sounded and the system is disabled to alert the operator of the presence of a defective apparatus. As hereinbefore noted, other alarm conditions may be detected to alert the operator to a malfunction which is considered undesirable.

It should be noted that all of the operation of the valves and other electric components are set to fail safe. That is, in the absence of electricity or in the presence of a malfunction, the balloon 72 is deflated and injection of retroperfusate is interrupted. Thus, the maximum coronary sinus pressure can never be obtained to impose pressure related damage in the coronary sinus region.

In laboratory experiments heretofore conducted, it has been noted that the application of the coronary sinus retroperfusion therapy as herein described using the apparatus and method hereinbefore disclosed produces a substantial benefit. That is, ischemia can be minimized and necrosis avoided in a substantial part of the effected myocardial tissue effected by a naturally occurring occlusion. The therapy can be effected continuously for a fairly extended period of time pending completion of other treatment procedures (e.g., a bypass).

It has been particularly noted that the retrograde perfusion therapy hereinbefore described can be enhanced in some situations when combined with intra-aortic balloon therapy. That is, a conventional aortic balloon catheter can be inserted into the aorta near the region of the heart and the balloon manipulated (inflate-deflate) on a repetitive basis to pump blood through the arterial system. Positioning of the aortic balloon pump downstream to those arteries that supply the heart results in a lower arterial pressure at the output of the heart which in turn can facilitate the degree of retroperfusion or retroperfusion upstream migration (i.e., lower back pressure) and the benefits of retrograde perfusion in the myocardial area.

It is to be understood that the embodiments of the instant invention herein described are merely illustrative of the application of the principals of the instant invention. Reference herein to details of the illustrated embodiment is not intended to limit the scope of the claims, which themselves recite those features regarded as essential to the invention.

We claim:

1. A catheter comprising:
   cannula means having a proximal end, a distal end in fluid communication with a corporeal lumen, and a channel for communication of fluids between said distal and proximal ends, said cannula means being formed for positioning within said corporeal lumen and for connection to external means when positioned in said corporeal lumen;
   balloon means attached to said cannula means proximate said distal end and operable between an inflated condition in which said balloon means substantially occludes said corporeal lumen and a deflated condition in which said balloon means is collapsed about said cannula means, said balloon means being sized and shaped to facilitate fluid flow therepast in said lumen when in said deflated condition;
   connector means attached to said proximal end for connection to a fluid reservoir;
   balloon inflating means associated with said cannula means for operating said balloon means between said inflated and deflated conditions, said balloon inflating means including a second channel formed in said cannula means and a port formed in said cannula means in fluid communication between said second channel and the interior of said balloon means; and
   pressure sensing means to sense the pressure of fluids within said lumen and communicate signals reflective thereof at said proximal end, said pressure sensing means including a port formed in said cannula means between said balloon means and said distal end and a third channel formed in said cannula means in fluid communication with said port to communicate fluid pressure signals therethrough.

2. The catheter of claim 1 wherein said balloon means in said inflated condition surrounds said cannula means and is shaped to be elongated and cigar-like with a taper toward said distal end.

3. The catheter of claim 2 wherein said taper is at an angle of less than about 40 degrees as between the exterior surface of said cannula means and the outer surface of said balloon means.

4. The catheter of claim 2 wherein said taper is at an angle between about 25 degrees and about 35 degrees as measured between the exterior surface of said cannula means and the outer surface of said balloon means.

5. The catheter of claim 2 wherein said balloon means is secured to said cannula means to form a plurality of essentially spiral ribs along said cannula means in said deflated condition.

6. The catheter of claim 2 wherein said cannula means includes a recess formed therein proximate said balloon means and wherein said balloon means in said deflated condition has portions thereof within said recess.

7. The catheter of claim 2 wherein said balloon is formed of a thin essentially inelastic material and wherein said balloon in said inflated condition tapers towards said proximal end at an angle of about 30 degrees as measured between the exterior surface of said cannula means and the outer surface of said balloon means.

8. The catheter of claim 2 wherein said cannula means includes pressure sensing means to sense the pressure of fluids within said lumen and communicate signals reflective thereof toward said distal end.

9. The catheter of claim 8 wherein said pressure sensing means includes a second port formed in said cannula means between said balloon means and said distal end and a third channel formed in said cannula means in fluid communication with said port to communicate fluid pressure signals therethrough to said proximal end.

10. A catheter comprising:
cannula means for communicating fluids between interior and exterior of a body, said cannula means having a distal end and a proximal end, said cannula means being sized in cross section to be positioned within a fluid transporting corporeal lumen and in length to extend from within the body to exterior thereof, and said cannula means having a first channel formed therein for communication of fluids between said distal end and said proximal end;
a balloon secured to said cannula means proximate said distal end and operable between an inflated condition in which said balloon is expanded to substantially occlude said corporeal lumen and a deflated condition in which said balloon is collapsed about said cannula means, said balloon being formed of a thin material and to have a cigar-like shape in the inflated condition with a taper toward both the proximal and distal ends at an angle of about 25 to about 35 degrees as measured between the exterior surface of the cannula means and the outer surface of said balloon;
connector means secured to said proximal end for connection to a fluid reservoir; and
a second channel formed in said cannula means in fluid communication with the balloon for operation thereof.

11. The catheter of claim 10 wherein said cannula means includes a recess formed therein proximate said balloon, wherein said balloon in said deflated condition has portions within said recess and wherein said balloon is formed of a substantially inelastic material.

12. A retrograde perfusion catheter comprising:
cannula means adapted to transport fluids from exterior the body to the coronary sinus region, said cannula means having distal and proximal ends and being sized to extend from exterior the body into a lumen of the coronary sinus region of the heart, said cannula means having a first channel formed therein for communication of said fluids into said coronary sinus region;
balloon means secured to said cannula means proximate to said distal end and operable between an inflated condition in which said balloon means surrounds said cannula means and is expanded to an elongated cigar-like shape with a taper toward said proximal and distal ends at an angle from about 25 degrees to about 35 degrees as measured between the exterior surface of said cannula means and the outer surface of said balloon means to substantially occlude fluid flow in said lumen and to a deflated condition in which said balloon means is collapsed about said cannula means, said balloon means being sizes and shaped to facilitate fluid flow therepast in said lumen when in said deflated condition;
connector means secured to said proximal end in fluid communication with said first channel for connection to a source of fluids;
balloon inflation means connected to said cannula means for operating said balloon means between said inflated and deflated conditions, said balloon inflating means including a second channel formed in said cannula means in fluid communication with the interior of said balloon means; and
pressure sensing means to sense the pressure of fluids within said lumen and communicate signals reflective thereof at said proximal end, said pressure sensing means including a port formed in said cannula means between said balloon means and said distal end and a third channel formed in said cannula means in fluid communication with said port to communicate fluid pressure signals therethrough.

13. The retrograde catheter of claim 12 wherein said balloon means is adapted to said cannula means to form a plurality of essentially spiral ribs along said cannula means in said deflated condition.

14. The catheter of claim 12 wherein said cannula means includes pressure sensing means to sense the pressure of fluids within said lumen and communicate signals reflective thereof at said proximal end.

15. The catheter of claim 12 wherein said source of fluids is a source of oxygenated blood.

16. A retrograde perfusion driver for connection to a retrograde perfusion catheter for communicating fluids into a fluid transporting corporeal lumen, which retrograde perfusion catheter has a distal end with an inflatable balloon positioned proximate thereto and a proximal end for connection to said driver, said retrograde perfusion driver comprising;
supply means in fluid communication with a said retrograde perfusion catheter to supply retroperfusate thereto and to supply operating signals to a said balloon positioned proximate the distal end of said retrograde perfusion catheter to cause said balloon to operate between an inflated condition and a deflated condition, said supply means including:

source means connectable to said retrograde perfusion catheter for supplying retroperfusate under pressure to said retrograde perfusion catheter, said source means including a supply of retroperfusate and pump means with an inlet connected to said supply of retroperfusate and an outlet connected to said retrograde perfusion catheter, and balloon operation means for connection to said retrograde perfusion catheter to supply said operating signals thereto, said balloon operation means including an operating signal generator connected to said retrograde perfusion catheter for supplying said operating signals and actuation means positioned proximate said operating signal generator for operation thereof, and wherein said second control signals are supplied to said actuation means;

control means for generating first and second control signals and connected to said supply means to supply said first control signals thereto to cause said source means to supply said retroperfusate under pressure, and connected to said balloon operation means to supply said second control signals thereto to cause supply of said operating signals, said first and second control signals being periodically generated in accordance with a preselected pattern.

17. The retrograde perfusion drive of claim 16 wherein said pump means comprises a roller and an electrical motor connected to drive said roller, and wherein said first control signals are power signals to operate said electrical motor.

18. The retrograde perfusion driver of claim 17 wherein said operating signal generator is a fluid pump to generate said operating signals which are fluid supplied to said balloon for inflation to said inflated condition and fluid extracted for deflation to said deflated condition.

19. The retrograde perfusion driver of claim 18 wherein said fluid pump is a syringe with a plunger, wherein said actuation means includes a member positioned proximate said plunger for movement thereof.

20. The retrograde perfusion driver of claim 19 wherein said actuation means comprises:

said member which is a lever pivotally mounted to rotate about an axis between an in position and an out position, said lever having a first end associated with said plunger for movement thereof and a second end;

an air operated piston having a shaft connected to said second end for movement thereof;

a source of pressurized air connected to supply pressurized air to said piston for operation of said shaft;

solenoid valve means interconnected between said source of pressured air and said piston to regulate the supply of said pressurized air; and wherein said control means is conductively connected to said solenoid valve means, and wherein said second control signal is an electrical signal to operate said solenoid valve means.

21. The retrograde perfusion driver of claim 19 wherein said retrograde perfusion catheter has means to detect the pressure in said lumen between the said balloon and said distal end and to communicate signals reflective thereof to said proximal end, said retrograde perfusion driver further including pressure detecting means connected to said proximal end to receive pressure signals reflective of fluid pressure therefrom and to output signals reflective of said pressure to said control means.

22. The retrograde perfusion driver of claim 21 wherein said control means includes means to receive said output signals from said pressure detecting means and means to compare said output signals with at least one preselected value reflective of a preselected pressure and to cause said second control signal to operate said solenoid to cause said balloon to operate between said inflated and deflated condition in relation to the output signals in accordance with a preselected program.

23. The retrograde perfusion driver of claim 22 wherein means to detect the pressure in said lumen of said retrograde perfusion catheter includes a second channel formed in said retrograde perfusion catheter in operative fluid communication with the said lumen, and wherein said pressure detecting means includes a source of flush fluid under pressure connected by means to supply flushing fluid through said pressure detecting means to said second channel.

24. The retrograde perfusion driver of claim 18 wherein said balloon operation means includes priming means connected to said control means to receive second control signals therefrom and connected to the outlet of said fluid pump, said priming means operating first to aspirate substantially all fluid from said balloon and the pump and to in sequence supply a metered amount of selected fluid thereto, all in accordance with a preselected program.

25. The retrograde perfusion driver of claim 24 wherein said selected fluid is a gas and wherein said priming means includes:

a source of said gas under pressure connected to said outlet;

a source of vacuum connected to said outlet;

second solenoid valve means interconnected between said source of said gas and source of said vacuum and conductively connected to said control means to receive said second control signals and operable to periodically and selectively connect said source of vacuum to said outlet and sequentially said source of said gas.

26. The retrograde perfusion driver of claim 25 wherein said priming means includes priming pressure sensing means to sense the pressure at the outlet of said fluid pump and supply signals reflective thereof to said control means, wherein said control means receives said pressure reflective signals from said priming pressure sensing means and compare them to preselected signals to cause generation of said second control signals to said second solenoid valve means.

27. The retrograde perfusion drive of claim 16 wherein said control means is positioned on a first chassis and said supply means is positioned on a second chassis remote from said first chassis.

28. A retrograde perfusion system comprising:

a catheter for communicating retroperfusate into a corporeal lumen, said catheter being formed to be positioned through a corporeal vein and into a lumen in the coronary sinus region of the heart, said catheter having:

a distal end and a proximal end, a first channel formed therein for communication of retroperfusate into said coronary sinus region, a balloon positioned about said catheter proximate said distal end and operable between an inflated condition in which said balloon is expanded to substantially occlude fluid flow in said lumen and a deflated condition in which said balloon is deflated about said catheter, said balloon being formed to have an elongated cigar-like shape with a taper toward said proximal end and toward said distal end each at an angle between about 25 degrees and about 35 degrees between the exterior surface of said catheter means and the outer surface of said balloon, a recess formed proximate said balloon wherein said balloon in said deflated condition has portions within said recess, and a second channel formed in said catheter in communication with the interior of said balloon;

a source of retroperfusate; and a driver comprised of:

a supply pump connected to said source of retroperfusate to receive retroperfusate therefrom and to said first channel to supply retroperfusate thereto and operable to pump the retroperfusate under pressure to and through said first channel into said lumen, balloon operation means connected to said second channel, said balloon operation means having a source of fluid and operable to supply and extract said fluid to and from said balloon through said second channel, control means conductively connected to said supply pump and said balloon operation means to supply control signals thereto, said control means having means to generate control signals to operate said supply pump and said balloon inflation means in accordance with a preselected program.

29. The retrovenous perfusion system of claim 28 wherein said balloon is formed to have an elongated cigar-like shape with a taper toward said proximal end and said distal end each at an angle between about 25 degrees and about 35 degrees between the exterior surface of said catheter means and the outer surface of said balloon.

30. The retrovenous perfusion system of claim 29 wherein said catheter means includes a recess formed therein proximate said balloon, and wherein said balloon in said deflated condition has portions within said recess.

31. The retrovenous perfusion system of claim 28 wherein said catheter includes a third channel formed therein in fluid communication with said lumen between said balloon and said distal end, and wherein said driver includes pressure sensing means connected to said third channel by means at said proximal end to sense the pressure of fluid therein and generate signals reflective thereof and connected to supply same to said control means.

32. The retrovenous perfusion of claim 31 wherein said control means includes means to select a first preset signal reflective of a maximum pressure, means to receive said pressure reflective signal from said pressure sensing means, and means to compare said pressure reflective signal from said pressure sensing means to said first preset signal and to supply a control signal to said balloon operation means to cause said balloon operation means to operate to deflate said balloon when the pressure reflective signal from said pressure sensing means exceeds said first preset signal.

33. The retrovenous perfusion of claim 32 wherein said control means includes means to select a second preset signal reflective of a minimum pressure, means to receive said pressure reflective signal from said pressure sensing means, and means to compare said pressure reflective signal from said pressure sensing means to said second preset signal and to supply a control signal to said balloon operating means to cause inflation of said balloon.

34. The retrovenous perfusion of claim 33 wherein said control means includes first and second timing means connected to measure the time said balloon is in a deflated condition and in an inflated condition respectively and means associated with said first timing means to select a first time for inflation and with said second timing means to select a second time for deflation, and wherein said first and second timing means are connected within control means to cause said balloon operation means to operate to cause said balloon to be placed in said deflated condition when said first time is measured and in said inflated condition when said second time is measured.

35. The retrovenous perfusion system of claim 31 wherein said control means has means to indicate the pressure sensed by said pressure sensing means.

36. The retrovenous perfusion system of claim 31 wherein said pressure sensing means further includes a source of flush fluid under pressure connected by means to supply flushing fluid through said pressure detecting means into said third channel.

37. The retrovenous perfusion system of claim 28 wherein said balloon operation means includes an operating signal generator to supply and extract said fluid and actuation means associated with said operating signal generator for operation thereof, and wherein said control signals are supplied to said actuation means.

38. The retrovenous perfusion system of claim 37 wherein said operating signal generator is a fluid pump.

39. The retrovenous perfusion system of claim 38 wherein said fluid pump is a syringe with a plunger, wherein said actuation means includes a member positioned proximate with said plunger for movement thereof and means associated with said member for movement thereof.

40. The retrovenous perfusion system of claim 39 wherein said actuation means includes:

said member which is a lever pivotally mounted to rotate about an axis between an in position and an out position, said lever having its first end associated with said plunger for movement thereof and a second end;

an air operated piston having a shaft connected to said second end for movement thereof;

a source of pressurized air connected to supply pressurized air to said piston for movement of said shaft;

solenoid valve means interconnected between said source of pressurized air and said air operated piston to regulate the supply of said pressurized air;

wherein said control means is conductively connected to said solenoid valve means; and wherein said control signals include an electrical signal to operate said solenoid valve means.

41. The retrovenous perfusion system of claim 28 wherein said supply pump includes pumping structure and an electric motor connected thereto for operating said pumping structure, and wherein said control means has means to supply electrical power to said electric motor for operation thereof and wherein said control means includes a source of electrical power.

42. The retrovenous perfusion system of claim 41 wherein said source of electrical power includes connection means switchable between an internal battery and an external source of electrical power.

43. The retrovenous perfusion system of claim 28 wherein said balloon operation means includes priming means connected by means to said second channel and operable to remove fluid from said second channel and balloon, and to sequentially fill said second channel and said balloon with a fluid.

44. A retrovenous perfusion system comprising:
a catheter for communicating retroperfusate into a corporeal lumen, said catheter being formed to be positioned through a corporeal vein and into a lumen in the coronary sinus region of the heart, said catheter having:
a distal end and a proximal end,
a first channel formed in said catheter for communication of retroperfusate into said coronary sinus region,
a balloon secured to said catheter proximate said distal end and operable between an inflated condition in which said balloon is expanded to substantially occlude fluid flow in said lumen and a deflated condition in which said balloon is deflated about said catheter,
a second channel formed in said catheter in communication with the interior of said balloon,
a recess formed in said catheter proximate said balloon wherein said balloon in said deflated condition has portions within said recess,
a third channel formed in said catheter in fluid communication with said lumen between said balloon and said proximal end, and
wherein said balloon is formed to have elongated cigar-like shape with a taper toward said distal and proximal ends;
a source of retroperfusate;
a driver having:
pressure sensing means connected to said third channel to sense the pressure of fluid therein and to generate signals reflective thereof,
supply pump means connected to said first channel and to said source of retroperfusate to receive and to supply retroperfusate to said first channel under pressure,
motor means associated with said supply pump means to operate said supply pump means,
a pump comprised of a syringe with a plunger and having an outlet connected to said second channel and to a source of fluid and
actuation means associated with said pump for operation thereof;
control means conductively connected to receive said pressure reflective signals from said pressure sensing means to said solenoid valve means to supply control signals thereto and to said motor means to supply operation signals thereto, said control means having:
first means to select a first preset signal reflective of a maximum pressure, means to receive said pressure reflective signal from said pressure sensing means, and means to compare said pressure reflective signal from said pressure sensing means to said first preset signal and to supply a control signal to said actuation to cause said actuation to operate said pump to deflate said balloon when the pressure reflective signal from said pressure sensing means exceeds said first preset signal,
second means to select a second preset signal reflective of a minimum pressure, means to receive said pressure reflective signal from said pressure sensing means, and means to compare said pressure reflective signal from said pressure sensing means to said second preset signal and to supply a control signal to said actuation means to operate said pump to cause inflation of said balloon,
timing means connected to said first means and said second means to measure the time said balloon is in a deflated condition and in an inflated condition and means associated with said timing means to select a first time for inflation and a second time for deflation, and wherein said timing means is connected to said actuation means to cause said actuation means to operate to cause said balloon to be placed in said deflated condition when said first time is measured and in said inflated condition when said second time is measured; and
power supply means connected to supply electrical power to said control means.

45. The retrovenous perfusion system of claim 44 further including a source of flush fluid under pressure connected by means to supply flushing fluid through said pressure detecting means into said second channel.

46. The retrovenous perfusion system of claim 45 further including priming means having:
a source of gas under pressure connected to the outlet of said pump;
a source of vacuum connected to said outlet of said pump;
valve means interconnected between said source of said gas under pressure and said source of vacuum and operatively connected to said control means to receive said control signals and operable to periodically and selectively connect said source of vacuum to said outlet and sequentially said source of said gas.

47. A method of retrograde perfusion comprising:
inserting a catheter into a corporeal lumen, said catheter having a distal end and a proximal end, a first channel formed therein for communication of fluids between said distal end and said proximal end, and a balloon positioned proximate said distal end;
connecting a source of retroperfusate under pressure to said first channel;
inflating said balloon with a fluid through a second channel formed in said catheter to occlude said lumen for a first preselected period of time;
supplying said retroperfusate under pressure through said first channel into said lumen;
deflating said balloon by extracting said fluid from said balloon through said second channel to place the balloon in a deflated condition collapsed about said catheter for a second preselected period of time;
wherein said first preselected period of time is the first occurring of a preset time period of the attachment of a preselected pressure in said lumen proximate the said distal end; and
wherein said second preselected period of time is the first occurring of a preset time period or the attainment of a preselected pressure in said lumen proximate the said distal end.

48. The method of claim 47 further comprising inserting an intraaortic balloon pump into the patient, positioning the pumping structure proximate the heart, and operating said intraaortic balloon pump.

49. The method of claim 47 wherein said preselected pressures and times are selected by first inflating said balloon and measuring the pressure in said lumen proximate said distal end, supplying retroperfusate under pressure into said lumen and measuring the pressure in said lumen proximate said distal end, thereafter graphing the measured pressures versus time, and selecting a time and a pressure to ensure first retrograde perfusion of retroperfusate and thereafter a time and pressure for assuring desired drainage through said lumen.

50. A catheter comprising:
cannula means having a proximal end, a distal end in fluid communication with a corporeal lumen, and a channel for communication of fluids between said distal and proximal ends, said cannula means being sized and shaped for positioning within said corporeal lumen and for connection to external means when positioned in said corporeal lumen;
a balloon secured to said cannula means proximate said distal end and operable between an inflated condition in which said balloon means substantially occludes said corporeal lumen and a deflated condition in which said balloon is collapsed about said cannula means, and forms a plurality of essentially spiral ribs along said cannula means;
connector means secured to said proximal end for connection to a fluid reservoir; and
balloon inflating means associated with said cannula means for operating said balloon means between said inflated and deflated conditions.

51. A catheter comprising:
cannula means having a proximal end, a distal end in fluid communication with a corporeal lumen, and a channel for communication of fluids between said distal and proximal ends, said cannula means being sized and shaped for positioning within said corporeal lumen and for connection to external means when positioned in said corporeal lumen;
balloon means secured to said cannula means proximate said distal end and operable between an inflated condition in which said balloon means substantially occludes said corporeal lumen and a deflated condition in which said balloon means is collapsed about said cannula means,
a recess formed in said cannula means proximate said balloon means, a portion of said balloon means being within said recess in said deflated condition;
connector means secured to said proximal end for connection to a fluid reservoir; and
balloon inflating means associated with said cannula means for operating said balloon means between said inflated and deflated conditions.

* * * * *

UNITED STATES PATENT AND TRADEMARK OFFICE
CERTIFICATE OF CORRECTION

PATENT NO. : 5,024,668

DATED : JUNE 18, 1991

INVENTOR(S) : JEFFREY L. PETERS; JEFFREY L. ORTH

It is certified that error appears in the above-identified patent and that said Letters Patent is hereby corrected as shown below:

Col. 5, line 38, delete "6" and add ---6A---.

Col. 18, line 44, after "amplifier" and before "supplies" insert ---360---.

Col. 21, line 1, delete "operator" and add ---comparator---.

Col. 22, line 60, after "prime" insert ---)--- (right parenthesis).

Col. 24, line 5 and 30, delete "motorolla" and add ---Motorola---.

Col. 27, line 51, delete "leak" and add ---leaky---.

Col. 29, line 8, after "as" and before "between" insert ---measured---.

Col. 32, line 56, delete "drive" and add ---driver---.

Col. 36, line 64-65, delete "of the attachment" and add ---or the attainment---.

Col. 37, line 30, after "balloon" and before "is" insert ---means---.

UNITED STATES PATENT AND TRADEMARK OFFICE
CERTIFICATE OF CORRECTION

PATENT NO. : 5,024,668

DATED : June 18, 1991

INVENTOR(S) : JEFFREY L. PETERS: JEFFREY L. ORTH

It is certified that error appears in the above-identified patent and that said Letters Patent is hereby corrected as shown below:

Col. 30, line 66, delete "a".

Col. 31, line 31, delete "drive" and add ---driver---.

Col. 35, line 55, after "fluid" and before "and" insert ---,--- (comma).

Signed and Sealed this

Fifteenth Day of June, 1993

Attest:

MICHAEL K. KIRK

Attesting Officer

Acting Commissioner of Patents and Trademarks